(12) United States Patent
Honjo et al.

(10) Patent No.: US 11,302,438 B2
(45) Date of Patent: Apr. 12, 2022

(54) ANALYZING APPARATUS AND ANALYZING METHOD

(71) Applicant: CANON MEDICAL SYSTEMS CORPORATION, Otawara (JP)

(72) Inventors: Yasunori Honjo, Kawasaki (JP); Tetsuya Kawagishi, Nasushiobara (JP); Masaki Watanabe, Utsunomiya (JP)

(73) Assignee: CANON MEDICAL SYSTEMS CORPORATION, Otawara (JP)

( * ) Notice: Subject to any disclaimer, the term of this patent is extended or adjusted under 35 U.S.C. 154(b) by 100 days.

(21) Appl. No.: 16/591,669

(22) Filed: Oct. 3, 2019

(65) Prior Publication Data
US 2020/0111559 A1    Apr. 9, 2020

(30) Foreign Application Priority Data

Oct. 3, 2018 (JP) .............................. JP2018-188529
Oct. 1, 2019 (JP) .............................. JP2019-181189

(51) Int. Cl.
*G06T 7/00* (2017.01)
*G16H 30/40* (2018.01)
(Continued)

(52) U.S. Cl.
CPC ............ *G16H 30/40* (2018.01); *G06K 9/3208* (2013.01); *G06K 9/3233* (2013.01); *G06T 7/0012* (2013.01); *G16H 30/20* (2018.01)

(58) Field of Classification Search
CPC ....... A61B 5/7246; A61B 8/08; A61B 8/0891; A61B 8/5207; A61B 8/5223;
(Continued)

(56) References Cited

U.S. PATENT DOCUMENTS 6,985,172 B1 *  1/2006  Rigney et al. ..... G06K 9/00335
                                              348/149
2014/0147013 A1  5/2014  Shandas et al.
(Continued)

FOREIGN PATENT DOCUMENTS

JP       3109747 B2    11/2000
JP       4744833 B2     8/2011
(Continued)

OTHER PUBLICATIONS

Extended European Search Report dated Mar. 20, 2020 in European Patent Application No. 19201159.1, citing documents AA, AO, AP and AQ therein, 7 pages

*Primary Examiner* — Andrew W Johns
(74) *Attorney, Agent, or Firm* — Oblon, McClelland, Maier & Neustadt, L.L.P.

(57) ABSTRACT

An analyzing apparatus according to an embodiment includes processing circuitry. The processing circuitry acquires a plurality of time-series medical images. The processing circuitry calculates, for each of image pairs each formed of two medical images included in the medical images, a first index value indicating similarity between image signals in the two medical images. The processing circuitry also calculates, on the basis of a plurality of the first index values calculated for the respective image pairs, a second index value corresponding to a statistical value in a time direction of the first index values.

21 Claims, 17 Drawing Sheets

(51) Int. Cl.
*G16H 30/20* (2018.01)
*G06K 9/32* (2006.01)

(58) Field of Classification Search
CPC ........... G06K 9/00496; G06K 9/00536; G06K 9/0055; G06K 9/3233; G06K 9/6201; G06K 9/6202; G06K 9/6212; G06K 9/6215; G06T 7/0012; G06T 7/20; G06T 7/254; G16H 30/00; G16H 30/20; G16H 30/40; G16H 50/20
See application file for complete search history.

(56) References Cited

U.S. PATENT DOCUMENTS

| | | |
|---|---|---|
| 2014/0357990 A1 | 12/2014 | Wang |
| 2016/0307424 A1* | 10/2016 | Mills et al. ........ G06K 9/00771 |
| 2017/0278250 A1 | 9/2017 | Mikuriya et al. |
| 2018/0268574 A1* | 9/2018 | Lilja et al. ............ G06T 11/006 |

FOREIGN PATENT DOCUMENTS

| | | |
|---|---|---|
| JP | 5481407 B2 | 4/2014 |
| JP | 2017-174031 A | 9/2017 |
| WO | WO 2012/051216 A1 | 4/2012 |

\* cited by examiner

ANALYZING APPARATUS AND ANALYZING METHOD

CROSS-REFERENCE TO RELATED APPLICATIONS

This application is based upon and claims the benefit of priority from Japanese Patent Application No. 2018-188529, filed on Oct. 3, 2018 and Japanese Patent Application No. 2019-181189, filed on Oct. 1, 2019; the entire contents of which are incorporated herein by reference.

FIELD

Embodiments described herein relate generally to an analyzing apparatus and an analyzing method.

BACKGROUND

In conventional art, ultrasound contrast is used for recognition and diagnosis of angiomas. However, ultrasound contrast requires load on the subject and labor, and is difficult to introduce into routine examination. To recognize and diagnose angiomas by routine examination or the like, a technique enabling recognition by an imaging method using no contrast medium is required, such as B-mode imaging and Doppler mode imaging.

As characteristic findings of angiomas, it is known that echo intensity changes (fluctuates) for each time period. This is called "tubifex-like sign" or "wax and wane sign", or the like. Recognizing the findings may serve as an aid to recognition of angiomas. In addition, the findings described above are also recognized in other disease states, such as pus in a cyst, as well as angiomas. For this reason, the technique of recognizing the findings may be applied to diagnosis of other disease states.

DETAILED DESCRIPTION

An object to be solved with embodiments is to provide an analyzing apparatus and an analyzing method enabling evaluation of change of signal intensity of each time period.

An analyzing apparatus according to embodiments includes processing circuitry. The processing circuitry acquires a plurality of time-series medical images. The processing circuitry calculates, for each of image pairs each formed of two medical images included in the medical images, a first index value indicating similarity between image signals in the two medical images. The processing circuitry also calculates, on the basis of the first index values calculated for the respective image pairs, a second index value corresponding to a statistical value in the time direction of the first index values.

The following is an explanation of the analyzing apparatus and the analyzing method according to the embodiments, with reference to drawings. The following embodiments are not limited to the following explanation. In addition, the embodiments may be combined with other embodiments and/or conventional art within a range in which no contradiction occurs in the processing details.

Examples of the analyzing apparatus include a medical diagnostic apparatus and a medical information processing apparatus. Examples of the medical diagnostic apparatus include an ultrasonic diagnostic apparatus, an optical ultrasonic diagnostic apparatus (optoacoustic imaging apparatus), an X-ray diagnostic apparatus, an X-ray computed tomography (CT) apparatus, a magnetic resonance imaging (MRI) apparatus, a single photon emission computed tomography (SPECT) apparatus, a positron emission computed tomography (PET) apparatus, a SPECT-CT apparatus obtained by uniting a SPECT apparatus with an X-ray CT apparatus, a PET-CT apparatus obtained by uniting a PET apparatus with an X-ray CT apparatus, and a group of these apparatuses. Examples of the medical information processing apparatus include a workstation and a picture archiving communication system (PACS) viewer.

First Embodiment

Figure 1:
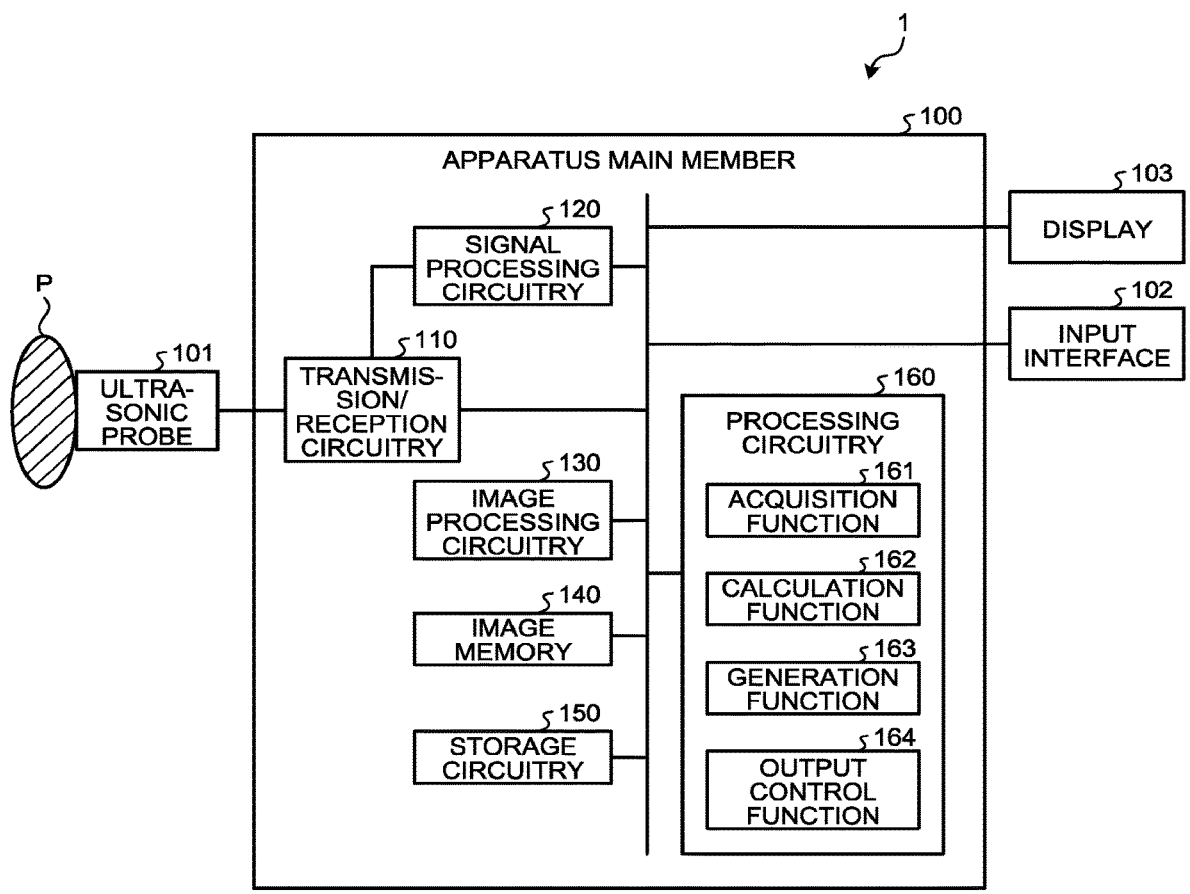
FIG. 1 is a block diagram illustrating a configuration example of an ultrasonic diagnostic apparatus according to a first embodiment.

FIG. 1 is a block diagram illustrating a configuration example of an ultrasonic diagnostic apparatus 1 according to a first embodiment. As illustrated in FIG. 1, the ultrasonic diagnostic apparatus 1 according to the first embodiment includes an apparatus main member 100, an ultrasonic probe 101, an input interface 102, and a display 103. The ultrasonic probe 101, the input interface 102, and the display 103 are connected with the apparatus main member 100 to be enabled to communicate with the apparatus main member 100. The subject P is not included in the configuration of the ultrasonic diagnostic apparatus 1. The ultrasonic diagnostic apparatus 1 is an example of the analyzing apparatus.

The ultrasonic probe 101 includes a plurality of transducer elements (for example, piezoelectric transducer elements). The transducer elements generate ultrasonic waves on the basis of drive signals supplied from transmission/reception circuitry 110 included in the apparatus main member 100 described later. The transducer elements included in the ultrasonic probe 101 receive reflected waves from the subject P, and convert the reflected waves into electrical signals. The ultrasonic probe 101 also includes matching layers provided in the transducer elements, and a backing material preventing backward propagation of ultrasonic waves from the transducer elements.

When ultrasonic waves are transmitted from the ultrasonic probe 101 to the subject P, the transmitted ultrasonic waves are successively reflected with an acoustic impedance discontinuous plane in the tissue in the body of the subject P, and received as reflected wave signals (echo signals) with the transducer elements included in the ultrasonic probe 101. The amplitudes of the received reflected waves depend on a difference in acoustic impedance in the discontinuous plane with which the ultrasonic waves are reflected. The reflected wave signals in the case where the transmitted ultrasonic pulses are reflected with a surface of the moving blood flow and/or a cardiac wall or the like are frequency-shifted, depending on the velocity component for the ultrasonic transmission direction of the moving object, by the Doppler effect.

The first embodiment is applicable to each of the case where the ultrasonic probe 101 illustrated in FIG. 1 is a one-dimensional ultrasonic probe in which a plurality of piezoelectric transducer elements are arranged in a line, the case where the ultrasonic probe 101 is a one-dimensional ultrasonic probe in which a plurality of piezoelectric transducer elements are mechanically oscillated, and the case where the ultrasonic probe 101 is a two-dimensional ultrasonic probe in which a plurality of piezoelectric transducer elements are two-dimensionally arranged in a lattice manner.

The input interface 102 corresponds to a mouse, a keyboard, a button, a panel switch, a touch command screen, a foot switch, a trackball, and/or a joystick, and the like. For example, the input interface 102 receives various setting requests from the operator of the ultrasonic diagnostic apparatus 1, and transfer the received various setting requests to the apparatus main member 100.

The display 103 displays a graphical user interface (GUI) to input various setting requests by the operator of the ultrasonic diagnostic apparatus 1 using the input interface 102, and displays ultrasonic image data generated in the apparatus main member 100.

The apparatus main member 100 is an apparatus generating ultrasonic image data on the basis of reflected wave signals received with the ultrasonic probe 101. As illustrated in FIG. 1, the apparatus main member 100 includes transmission/reception circuitry 110, signal processing circuitry 120, image processing circuitry 130, an image memory 140, storage circuitry 150, and processing circuitry 160. The transmission/reception circuitry 110, the signal processing circuitry 120, the image processing circuitry 130, the image memory 140, the storage circuitry 150, and the processing circuitry 160 are connected to be enabled to perform mutual communications.

The transmission/reception circuitry 110 includes a pulse generator, a transmission delay unit, and a pulser and the like, and supplies a drive signal to the ultrasonic probe 101. The pulse generator repeatedly generates rate pulses to form transmission ultrasonic waves at predetermined rate frequency. The transmission delay unit converges the ultrasonic waves generated from the ultrasonic probe 101 into a beam, and provides delay time for each of the piezoelectric transducer elements necessary for determining transmission directivity to each of the rate pulses generated with the pulse generator. The pulser applies a drive signal (drive pulse) to the ultrasonic probe 101 at a timing based on the rate pulse. Specifically, the transmission delay unit regulates, as desired, the transmission direction of the ultrasonic waves transmitted from the piezoelectric transducer surfaces, by changing the delay time provided to each of the rate pulses.

The transmission/reception circuitry 110 includes a function to enable instantaneous change of the transmission frequency and/or the transmission drive voltage and the like, to execute a predetermined scan sequence, on the basis of an instruction of the processing circuitry 160 described later. In particular, change of the transmission drive voltage is achieved with a linear-amplifier type transmission circuitry capable of instantaneously changing the value thereof, or a mechanism to electrically switching a plurality of power units.

The transmission/reception circuitry 110 also includes a preamplifier, an analog/digital (A/D) converter, a reception delay unit, and/or an adder, and the like, to perform various types of processing on the reflected wave signals received with the ultrasonic probe 101 and generate reflected wave data. The preamplifier amplifies the reflected wave signals for each of channels. The A/D converter performs A/D conversion on the amplified reflected wave signals. The reception delay unit provides delay time necessary for determining reception directivity. The adder performs addition processing on the reflected wave signals processed with the reception delay unit to generate reflected wave data. The addition processing performed with the adder emphasizes reflection components in a direction corresponding to the reception directivity of the reflected wave signals, and a comprehensive beam of ultrasonic transmission/reception is formed on the basis of the reception directivity and the transmission directivity.

The transmission/reception circuitry 110 transmits an ultrasonic beam in a two-dimensional direction from the ultrasonic probe 101, in the case of scanning a two-dimensional region of the subject P. The transmission/reception circuitry 110 generates two-dimensional reflected wave data from the reflected wave signals received with the ultrasonic probe 101. The transmission/reception circuitry 110 transmits an ultrasonic beam in a three-dimensional direction from the ultrasonic probe 101, in the case of scanning a three-dimensional region of the subject P. The transmission/ reception circuitry 110 generates three-dimensional reflected wave data from the reflected wave signals received with the ultrasonic probe 101.

The signal processing circuitry 120 performs, for example, logarithmic amplification and/or envelope detection on the reflected wave data received from the transmission/reception circuitry 110, to generate data (B-mode data) in which signal intensity for each of sample points is expressed with degree of luminance. The B-mode data generated with the signal processing circuitry 120 is output to the image processing circuitry 130.

The signal processing circuitry 120 generates, for example, data (Doppler data) obtained by extracting movement information based on the Doppler effect of the moving object, at each of sample points in the scanning region, from the reflected wave data received from the transmission/reception circuitry 110. Specifically, the signal processing circuitry 120 generates data (Doppler data) obtained by performing frequency analysis on velocity information from the reflected wave data, extracting the blood flow and/or the tissue, and contrast medium echo components by the Doppler effect, and extracting moving object information, such as the average velocity, dispersion, and power, for multiple points. The moving object is, for example, a blood flow, a tissue, such as a cardiac wall, and/or a contrast medium. The movement information (blood flow information) acquired with the signal processing circuitry 120 is transmitted to the image processing circuitry 130, and displayed with color on the display 103, as an average velocity image, a dispersion image, a power image, or a combination image thereof.

The image processing circuitry 130 generates ultrasonic image data from the data generated with the signal processing circuitry 120. The image processing circuitry 130 generates B-mode image data, in which intensities of the reflected waves are expressed by luminance, from the B-mode data generated with the signal processing circuitry 120. The image processing circuitry 130 also generates Doppler image data expressing moving object information from the Doppler data generated with the signal processing circuitry 120. The Doppler image data is velocity image data, dispersion image data, power image data, or image data serving as a combination thereof.

The image processing circuitry 130 generally converts (scan-converts) scanning line signal strings of ultrasonic scanning into scanning line signal strings of a video format represented by televisions and the like, to generate display ultrasonic image data. Specifically, the image processing circuitry 130 performs coordinate transformation according to the ultrasonic scanning form performed with the ultrasonic probe 101, to generate display ultrasonic image data. The image processing circuitry 130 also performs, for example, image processing (smoothing) to regenerate a mean value image of luminance and/or image processing (edge enhancement processing) using a differential filter in the image, using scan-converted image frames, as various image processing other than scan convert. The image processing circuitry 130 also synthesizes accessory information (such as character information of various parameters, a scale, and a body mark) with the ultrasonic image data.

Specifically, the B-mode data and the Doppler data are ultrasonic image data before scan convert processing, and data generated with the image processing circuitry 130 is display ultrasonic image data after scan convert processing. When the signal processing circuitry 120 generates three-dimensional data (three-dimensional B-mode data and three-dimensional Doppler data), the image processing circuitry 130 performs coordinate transformation in accordance with ultrasonic wave scanning form performed with the ultrasonic probe 101, to generate volume data. The image processing circuitry 130 performs various rendering processing on the volume data, to generate display two-dimensional image data.

The image memory 140 is a memory storing therein display images generated with the image processing circuitry 130. The image memory 140 is also capable of storing therein data generated with the signal processing circuitry 120. The B-mode data and/or the Doppler data stored in the image memory 140 can be called by the operator, for example, after diagnosis, and serve as display ultrasonic image data through the image processing circuitry 130. In the present embodiment, the simple expression "image" includes not only display images in which colors are assigned to the pixels but also a data string (also referred to as "image data") in which coordinates of the pixels are associated with the respective pixel values (signal values).

The storage circuitry 150 stores therein control programs to perform ultrasonic transmission/reception, image processing, and display processing, diagnostic information (such as the patient ID and the doctor's comments), and/or various data, such as diagnostic protocol and various body marks. The storage circuitry 150 is also used for storing therein image data stored in the image memory 140, when necessary. The data stored in the storage circuitry 150 may be transferred to an external device trough a communication interface (not illustrated).

The processing circuitry 160 controls the whole process of the ultrasonic diagnostic apparatus 1. Specifically, the processing circuitry 160 controls processing performed with the transmission/reception circuitry 110, the signal processing circuitry 120, and the image processing circuitry 130, on the basis of various setting requests input by the operator through the input interface 102 and/or the control programs and the various data read from the storage circuitry 150. The processing circuitry 160 also performs control to display the display ultrasonic image data stored in the image memory 140 on the display 103.

In addition, as illustrated in FIG. 1, the processing circuitry 160 executes an acquisition function 161, a calculation function 162, a generation function 163, and an output control function 164. The calculation function 162 is an example of a calculation unit. The generation function 163 is an example of a generation unit. The output control function 164 is an example of an output control unit.

For example, the storage device (for example, the storage circuitry 150) of the ultrasonic diagnostic apparatus 1 stores therein each of processing functions executed with the acquisition function 161, the calculation function 162, the generation function 163, and the output control function 164 serving as constituent elements of the processing circuitry 160 illustrated in FIG. 1, in the form of computer programs executable with a computer. The processing circuitry 160 is a processor reading the computer programs from the storage device and achieving functions corresponding to the computer programs by executing the computer programs. In other words, the processing circuitry 160 in the state of reading each of the computer programs have each of the functions illustrated in the processing circuitry 160 in FIG. 1. Each of the functions executed with the acquisition function 161, the calculation function 162, the generation function 163, and the output control function 164 will be described later.

The "change (fluctuations) of signal intensity of each time period" known as characteristic findings of angiomas may be expressed with, for example, fluctuations (standard deviations) of signal intensity in the frame direction (time direction). In this case, because the fluctuations increase as the signal intensity increases, normalization with the signal intensity itself is required. However, performing normalization (specifically, the fluctuations are converted into change rate), change of signal intensity increases at low luminance and easily fluctuates. Specifically, the standard deviation has values depending on the signal intensity. For this reason, it is considered that it is important to define the index value indicating change of signal intensity of each time period without dependence on signal intensity.

For this reason, in the present embodiment, when the index value indicating change of signal intensity of each time period, the two points are noted. The two points are "strength of correlation between frames" and "relation of correlations in the frame direction".

Figure 2:
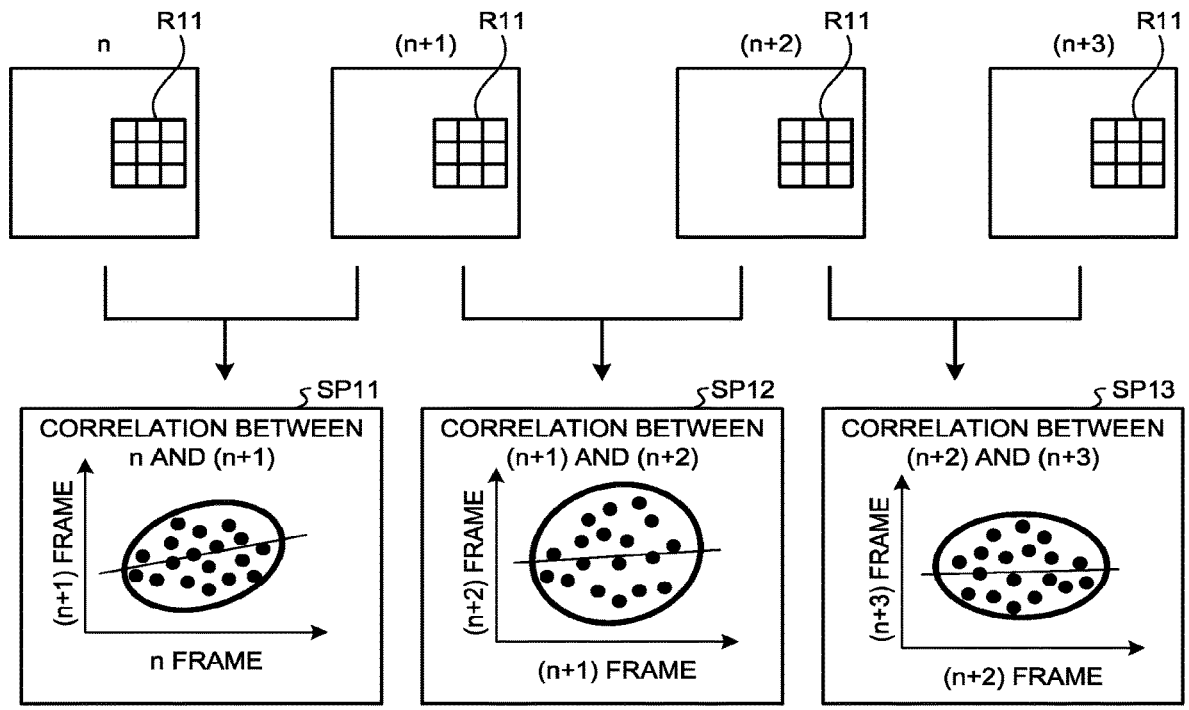
FIG. 2 is a diagram illustrating points to be noted according to the first embodiment.
Figure 3:
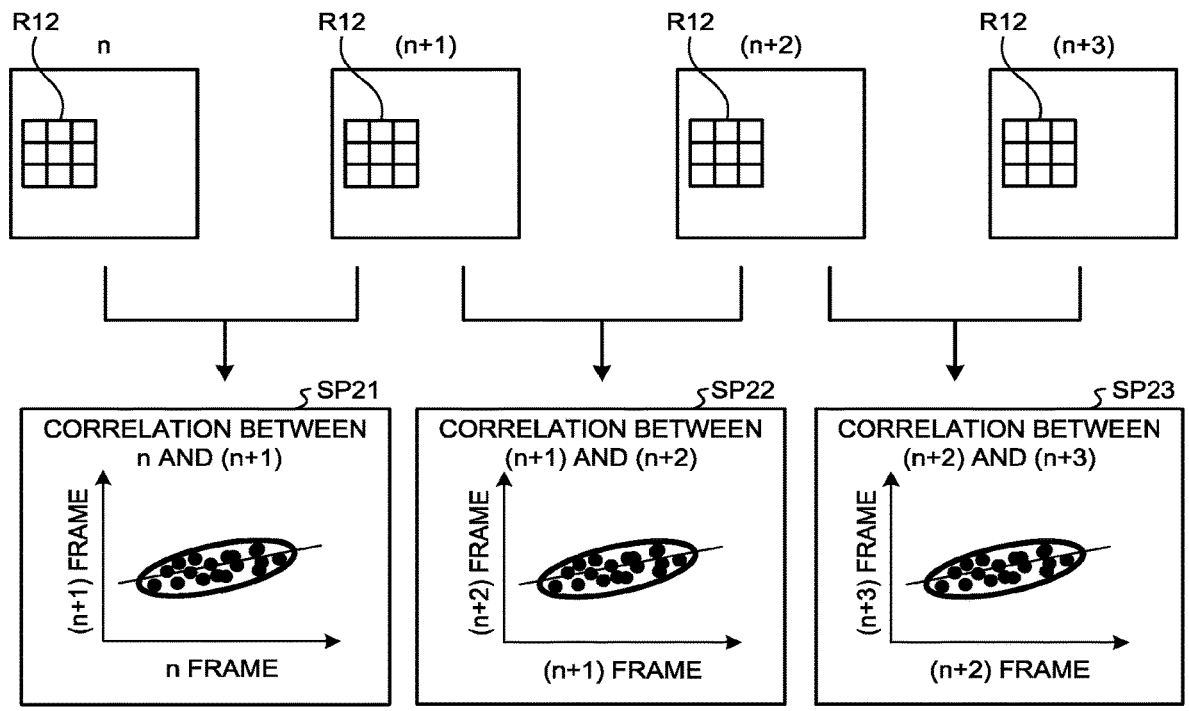
FIG. 3 is a diagram illustrating points to be noted according to the first embodiment.

The points to be noted according to the first embodiment will be explained hereinafter with reference to FIG. 2 and FIG. 3. FIG. 2 and FIG. 3 are diagrams for explaining the points to be noted according to the first embodiment. FIG. 2 and FIG. 3 illustrate correlation of distribution of pixel values between adjacent frames for a plurality of medical images arranged in time series. In FIG. 2 and FIG. 3, suppose that the whole movement (displacement) of the tissue between the medical images does not exist, or is corrected.

FIG. 2 illustrates correlation in the case where change of signal intensity (pixel value) of each time period exists. Scatter diagrams SP11, SP12, and SP13 illustrated in FIG. 2 are obtained by plotting points corresponding to respective pixel positions in a kernel (analyze window) set in a region R11 fluctuating in the frame direction. Specifically, the horizontal axis of the scatter diagram SP11 corresponds to the pixel value of the nth frame, and the vertical axis corresponds to the pixel value of the (n+1)th frame. The horizontal axis of the scatter diagram SP12 corresponds to the pixel value of the (n+1)th frame, and the vertical axis corresponds to the pixel value of the (n+2)th frame. The horizontal axis of the scatter diagram SP13 corresponds to the pixel value of the (n+2)th frame, and the vertical axis corresponds to the pixel value of the (n+3)th frame.

FIG. 3 illustrates correlation in the case where no change of signal intensity (pixel value) of each time period exists. Scatter diagrams SP21, SP22, and SP23 illustrated in FIG. 3 are obtained by plotting points corresponding to respective pixel positions in a kernel set in a region R12 having no fluctuation in the frame direction. Specifically, the horizontal axis of the scatter diagram SP21 corresponds to the pixel value of the nth frame, and the vertical axis corresponds to the pixel value of the (n+1)th frame. The horizontal axis of the scatter diagram SP22 corresponds to the pixel value of the (n+1)th frame, and the vertical axis corresponds to the pixel value of the (n+2)th frame. The horizontal axis of the scatter diagram SP23 corresponds to the pixel value of the (n+2)th frame, and the vertical axis corresponds to the pixel value of the (n+3)th frame.

For example, because change of signal intensity of each time period exists in a region in which an angioma exists, the correlation as illustrated in FIG. 2 is observed. Even in the same pixel position, the pixel value changes between the adjacent frames. For this reason, the scatter diagrams SP11, SP12, and SP13 of FIG. 2 have dispersion in a wider area (region in a shape close to a perfect circle) than those in the scatter diagrams SP21, SP22, and SP23 of FIG. 3. Specifically, it can be said that "correlation between frames is weak" in a region in which an angioma exists. In addition, with certain degree of change of the pixel value, correlation between frames may become temporarily strong. For example, because points in the scatter diagram SP13 are concentrated in a region (elongated oval region) narrower than that of the scatter diagram SP12, the scatter diagram SP13 has strong correlation. Specifically, it can be said that "correlation changes in the frame direction" in a region in which an angioma exists.

By contrast, in a region in which no angioma exists, that is, in a region in which background liver and/or a tumor other than angiomas exist, no change of signal intensity of each time period exists, and correlation as illustrated in FIG. 3 is observed. Because the pixel value has small change in the same pixel position between the adjacent frames, the points in the scatter diagrams SP21, SP22, and SP23 of FIG. 3 are concentrated in a narrower region (elongated oval region) than those of the scatter diagrams SP11, SP12, and SP13 of FIG. 2. Specifically, it can be said that "correlation between frames is strong" in a region in which no angioma exists. In addition, correlation is maintained strong in the scatter diagrams SP21, SP22, and SP23 of FIG. 3. Specifically, it can be said that "the correlation is fixed in the frame direction" in a region in which no angioma exists.

When the two points to be noted are summarized, it can be said that the following features exist according to presence/absence of angiomas. Specifically, regions in which an angioma exists have features "correlation between frames is weak" and "correlation changes in the frame direction". In addition, regions in which no angioma exists have features "correlation between frames is strong" and "correlation is fixed in the frame direction".

For this reason, the ultrasonic diagnostic apparatus 1 according to the first embodiment executes the following processing functions to output index values using these two points to be noted.

The following embodiment illustrates the case of evaluating fluctuations of an angioma drawn in the B-mode image, but the structure is not limited thereto. For example, the disclosed technique enables quantitative evaluation of any change of the tissue exhibiting fluctuations in the frame direction in the image, as well as angiomas. In addition, the disclosed technique is capable of evaluating not only B-mode images but also fluctuations in other ultrasonic images, such as Doppler images, or medical images imaged with other medical image diagnostic apparatuses.

Figure 4:
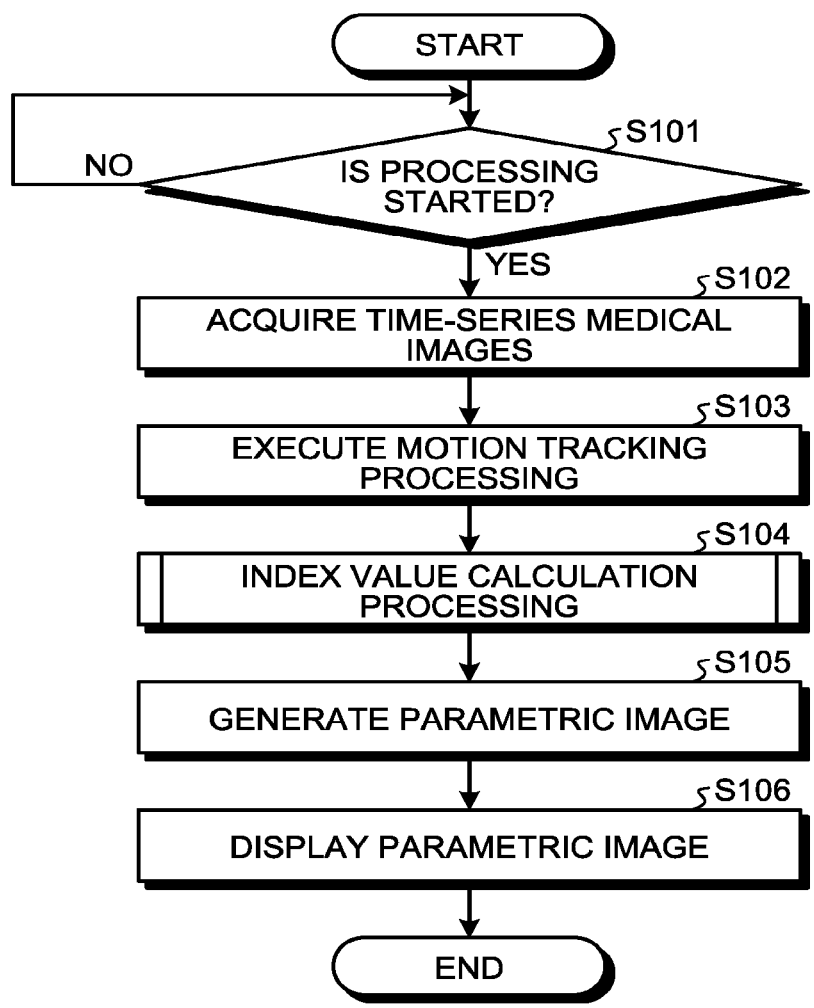
FIG. 4 is a flowchart illustrating a process performed with the ultrasonic diagnostic apparatus according to the first embodiment.
Figure 5:
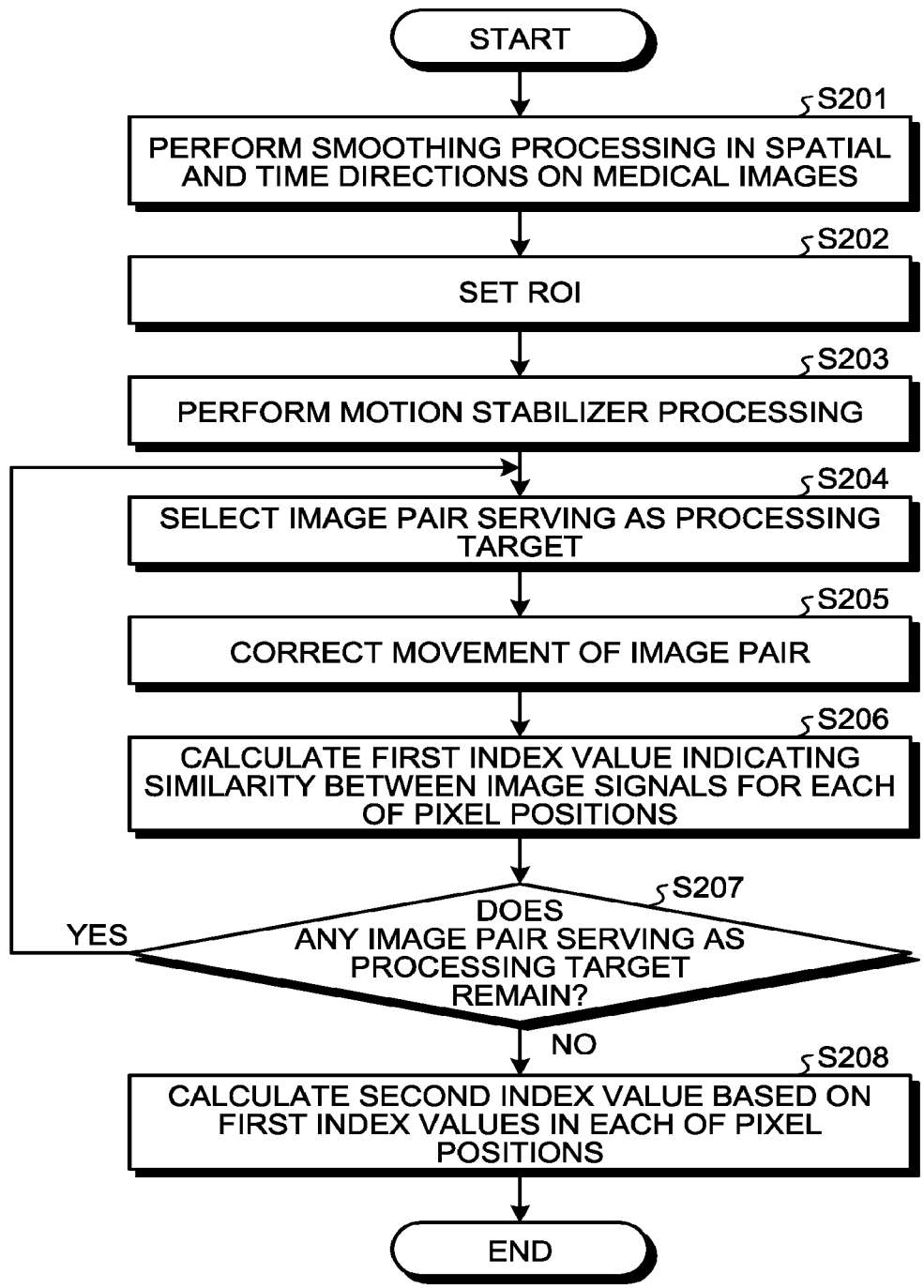
FIG. 5 is a flowchart illustrating a process of index value calculation processing according to the first embodiment.

The following is an explanation of a process performed with the ultrasonic diagnostic apparatus 1 according to the first embodiment with reference to FIG. 4 and FIG. 5. FIG. 4 is a flowchart illustrating a process performed with the ultrasonic diagnostic apparatus 1 according to the first embodiment. FIG. 5 is a flowchart illustrating a process of index value calculation processing according to the first embodiment. The process illustrated in FIG. 4 is started, for example, when an instruction to display a parametric image is received from the operator. The process illustrated in FIG. 5 corresponds to processing details at Step S104 illustrated in FIG. 4.

Figure 6:
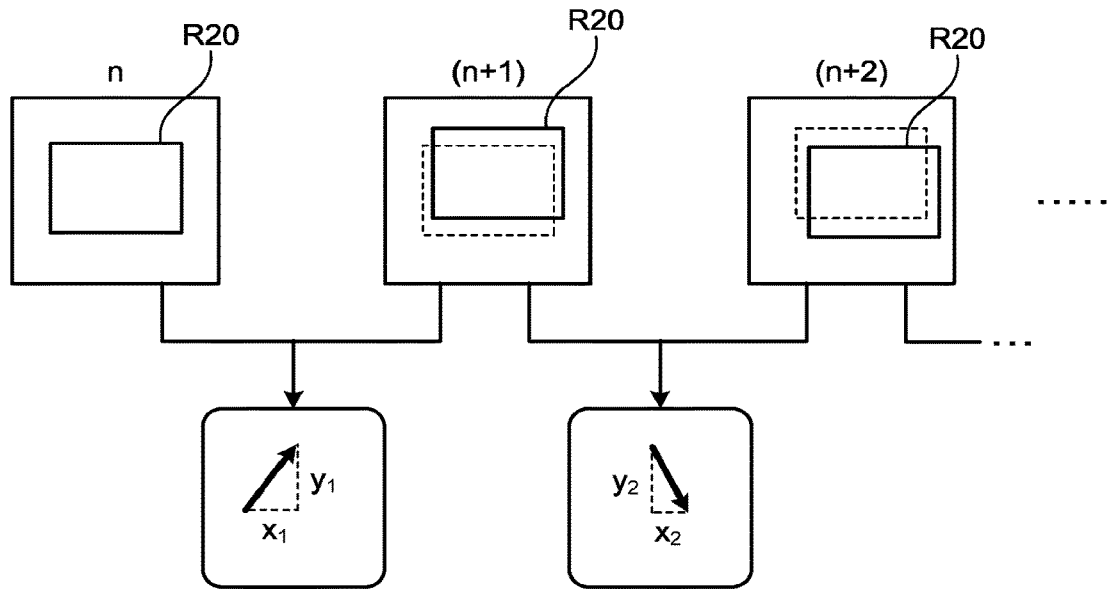
FIG. 6 is a diagram for explaining motion stabilizer processing according to the first embodiment.
Figure 7:
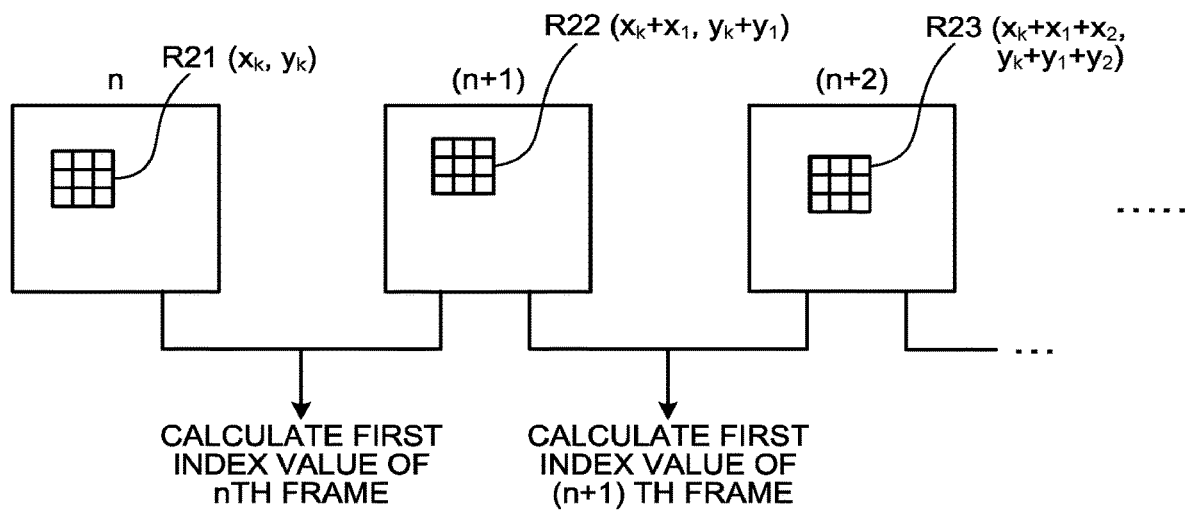
FIG. 7 is a diagram for explaining processing of calculating a first index value according to the first embodiment.
Figure 8:
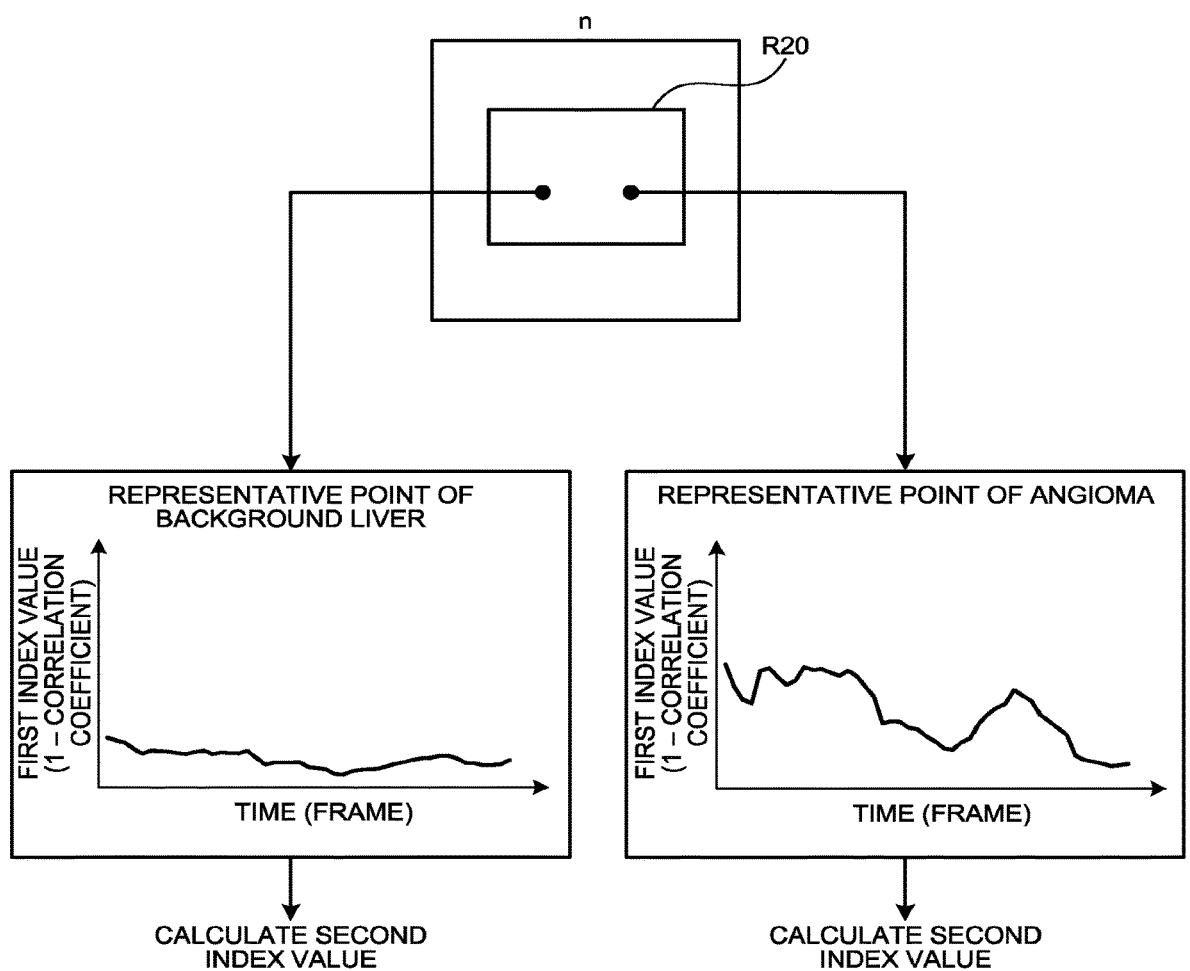
FIG. 8 is a diagram for explaining processing of calculating a second index value according to the first embodiment.
Figure 9:
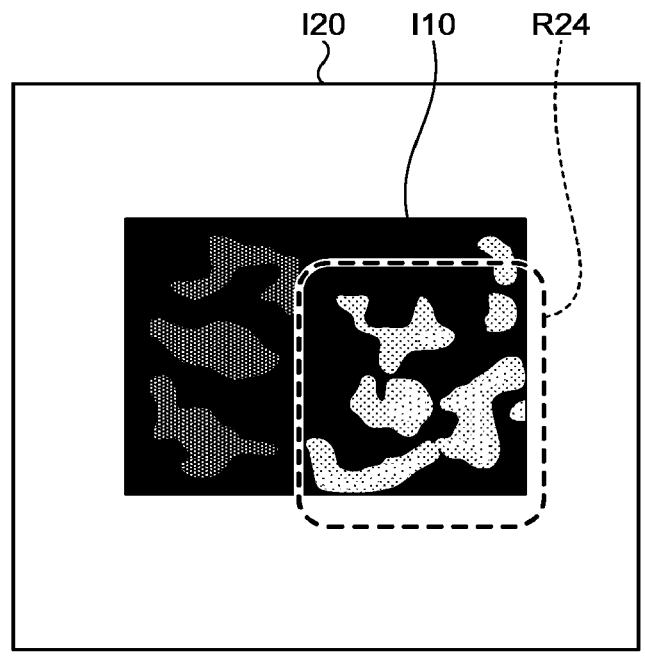
FIG. 9 is a diagram illustrating an example of a parametric image according to the first embodiment.

The following explanation is made with reference to FIG. 6 to FIG. 9. FIG. 6 is a diagram for explaining motion stabilizer processing according to the first embodiment. FIG. 7 is a diagram for explaining processing of calculating a first index value according to the first embodiment. FIG. 8 is a diagram for explaining processing of calculating a second index value according to the first embodiment. FIG. 9 is a diagram illustrating an example of a parametric image according to the first embodiment.

At Step S101, the processing circuitry 160 determines whether to start processing. For example, when an instruction to display a parametric image is received from the operator, the processing circuitry 160 determines to start processing (Yes at Step S101), and starts processing at Step S102 and the subsequent steps. When no processing is started (No at Step S101), no processing at Step S102 and the subsequent steps is started, and each of the processing functions is in a standby state.

When the answer at Step S101 is affirmative, the acquisition function 161 acquires a plurality of time-series medical images at Step S102. For example, the acquisition function 161 reads a plurality of time-phase B-mode image data arranged in a time-series manner from the image memory 140. As a specific example, the acquisition function 161 reads N pieces of B-mode image data from the first frame to the Nth frame from the image memory 140. Thereafter, the acquisition function 161 transmits the read N pieces of B-mode image data to the calculation function 162. The number N is a natural number. In the following processing, the B-mode image data corresponding to the whole scanning range subjected to ultrasonic scan may serve as the processing target, or only image data in the region of interest may serve as the processing target.

The following example illustrates the case where N pieces of B-mode image data have been imaged and stored in the image memory 140 in advance, but the embodiment is not limited thereto. For example, the acquisition function 161 may acquire N pieces of B-mode image data generated in real time. In this case, for example, the operator performs ultrasonic scan for N frames using the ultrasonic probe 101 after Step S101. The image processing circuitry 130 generates B-mode image data for N frames on the basis of B-mode data of N frames acquired by the ultrasonic scan. The acquisition function 161 acquires the generated B-mode image data for N frames from the image processing circuitry 130.

At Step S103, the calculation function 162 executes motion tracking processing on a plurality of medical images. For example, the read N pieces of B-mode image data include movement (displacement) between images due to camera shake and/or body movement (such as heartbeats). For this reason, the calculation function 162 performs motion tracking processing on the N pieces B-mode image data, to specify displacement between the medical images. The calculation function 162 corrects the specified displacement between the medical images, to generate a series of B-mode image data including no displacement in the frame direction. Publicly known motion tracking processing is properly applicable as the motion tracking processing.

At Step S104, the calculation function 162 executes index value calculation processing. The following is an explanation of processing at Step S201 to Step S208 executed as the index value calculation processing with reference to FIG. 5.

At Step S201, the calculation function 162 performs smoothing processing in the spatial direction and the time direction on the medical images. For example, the calculation function 162 performs low-pass filter (LPF) processing in the spatial direction on the N-sheets of B-mode images. For example, a moving average filter or a median filter is applicable in the LPF processing. In this manner, the calculation function 162 is enabled to reduce spike noise and/or speckle noise in the spatial direction.

The calculation function 162 also performs LPF processing on the N pixel values arranged in the time direction in the pixels of the N-sheets of B-mode images. In this manner, the calculation function 162 is enabled to reduce high-frequency noise, such as spike noise in the time direction, from the image signal intensity in the time direction. The calculation function 162 may perform either of LPF processing in the spatial direction and LPF processing in the time direction first, or may perform only one of them.

At Step S202, the calculation function 162 sets a region of interest (ROI). For example, the calculation function 162 displays one (typically, the image of the first frame) of the N-sheets of B-mode images having been subjected to smoothing processing on the display 103. The operator designates a region of a desired position and a desired size on the displayed B-mode image. The calculation function 162 sets the region designated by the operator on the B-mode image as the ROI. The calculation function 162 also sets a region of the same position and the same size as those of the ROI of the first frame in the other B-mode images (for example, the images of the second to the Nth frames).

The explanation herein illustrates the case where the ROI is manually set, but the ROI may be automatically set. For example, the calculation function 162 may extract the contour of the structure in the image by publicly known segmentation processing, and set a ROI in the image on the basis of the position and/or the shape of the extracted contour.

At Step S203, the calculation function 162 executes motion stabilizer processing. For example, displacement may remain even in the B-mode image subjected to displacement correction by the processing at Step S103. This occurs in the case where the region to be noted in execution of the motion stabilizer processing is different between Step S103 and Step S203. For example, at Step S103, a desired region is set as the region to be noted with respect to the positional relation between the background liver and the tumor, to correct the whole movement. By contrast, the processing at Step S203 is performed to correct and detect movement, such as beats, remaining in the removed whole movement, and it is recommended to note only the background liver side. When their regions to be noted are different, a difference (displacement) occurs in the position correction result. For this reason, the calculation function 162 performs motion stabilizer processing on the smoothed N-sheets of B-mode images, to correct or detect remaining displacement between the images. The regions to be noted at Step S103 and Step S203 described above are mere examples, and can be selected as desired.

The following is an explanation of the processing at Step S203 with reference to FIG. 6. FIG. 6 illustrates processing in the case of detecting displacement of the ROI from the B-mode images of the nth frame, the (n+1)th frame, and the (n+2)th frame. In FIG. 6, a region R20 indicates the ROI. A rectangular region illustrated with a broken line indicates the position of the region R20 in the previous frame. Each of n, n+1, and n+2 is a number included in a range of 1 to N.

As illustrated in FIG. 6, for example, the calculation function 162 performs tracking processing including pattern matching for the region R20, to specify the position of the region R20 in each of the B-mode images.

The calculation function 162 detects displacement on the basis of a difference in position of the region R20 between the adjacent frames. For example, the calculation function 162 detects displacement $x_1$ in a horizontal direction between the nth frame and the (n+11)th frame and displacement $y_1$ in the vertical direction. The calculation function 162 also detects displacement $x_2$ in the horizontal direction between the (n+1)th frame and the (n+2)th frame and displacement $y_2$ in the vertical direction.

As described above, the calculation function 162 detects displacement between the images in the N-sheets of B-mode images. The motion stabilizer processing is an example of movement correction processing to correct movement between the images, and publicly known motion stabilizer processing is applicable. The same processing as the motion tracking processing as described above may be applied as the motion stabilizer processing.

At Step S204, the calculation function 162 selects an image pair serving as the processing target. For example, the calculation function 162 selects two B-mode images of the nth frame and the (n+1)th frame as an image pair serving as the processing target among the N sheets of B-mode images.

At Step S205, the calculation function 162 corrects movement of the image pair. For example, the calculation function 162 corrects movement (displacement) between the two medical images included in the image pair, on the basis of the displacement detected by the motion stabilizer processing.

At Step S206, the calculation function 162 calculates a first index value indicating similarity between the image signals for each of pixel positions. For example, the calculation function 162 calculates a first index value indicating similarity between image signals in two medical images for the image pair formed of the two medical images included in the medical images.

At Step S207, the calculation function 162 determines whether any image pair serving as the processing target remains. For example, when any unprocessed B-mode image exists in the N-sheets of B-mode images, the calculation function 162 determines that an image pair serving as the processing target remains (Yes at Step S207), and proceeds to the processing at Step S204. By contrast, when no unprocessed B-mode image exists in the N-sheets of B-mode images, the calculation function 162 determines that no image pair serving as the processing target remains (No at Step S207), and proceeds to the processing at Step S208.

Specifically, the calculation function 162 repeatedly performs the processing from Step S204 to Step S207 while changing the image pair serving as the processing target. The calculation function 162 successively selects image pairs, and successively calculates a first index value based on each of the image pairs.

The following is an explanation of the processing from Step S204 to Step S207 with reference to FIG. 7. FIG. 7 illustrates the processing in the case of calculating the first index values of the nth frame and the (n+1)th frame from the B-mode images of the nth frame, the (n+1)th frame, and the (n+2)th frame. In FIG. 7, a region R21, a region R22, and a region R23 indicate kernels (analyzing windows) set in the B-mode images of the nth frame, the (n+1)th frame, and the (n+2)th frame, respectively.

First, the following is an explanation of the case where the B-mode images of the nth frame and the (n+1)th frame are selected as an image pair serving as the processing target. In this case, the calculation function 162 sets a kernel for each of the two B-mode images of the nth frame and the (n+1)th frame. For example, the calculation function 162 sets a kernel (region R21) including a pixel position $(x_k, y_k)$ included in the ROI (region R20) and serving as the center, in the B-mode image of the nth frame. The displacement between the images of the nth frame and the (n+1)th frame is $(x_1, y_1)$. For this reason, the calculation function 162 sets a kernel (region R22) including a pixel position $(x_k+x_1, y_k+y_1)$ serving as the center in the B-mode image of the (n+1)th frame.

Thereafter, the calculation function 162 calculates the first index value of the nth frame on the basis of a correlation coefficient between the image signal in the kernel of the nth frame and the image signal in the kernel of the (n+1)th frame. For example, pixel indexes to identify the pixel positions are assigned to the respective pixel positions in the kernel. For this reason, the calculation function 162 calculates a correlation coefficient using the pixel values for the respective pixel indexes in the region R21 and the pixel values for the respective pixel indexes in the region R22 as bivariate data. Thereafter, the calculation function 162 calculates the first index value of the nth frame by subtracting the calculated correlation coefficient from "1".

The following is an explanation of the case where the B-mode images of the (n+1)th frame and the (n+2)th frame are selected as the image pair serving as the processing target. A kernel (region R22) has been set for the B-mode image of the (n+1)th frame in the previous calculation processing. For this reason, the calculation function 162 sets a kernel (region R23) corresponding to the region R22 for the B-mode image of the (n+2)th frame. For example, the center position of the kernel (region R22) of the (n+1)th frame is $(x_k+x_1, y_k+y)$, and the displacement between the images of the (n+1) frame and the (n+2) frame is $(x_2, y_2)$. For this reason, the calculation function 162 sets a kernel (region R23) with the pixel position $(x_k+x_1+x_2, y_k+1+y_2)$ of the B-mode image of the (n+2)th frame serving as the center.

Thereafter, the calculation function 162 calculates the first index value of the (n+1)th frame on the basis of a correlation coefficient between the image signal in the kernel of the (n+1)th frame and the image signal in the kernel of the (n+2)th frame. For example, the calculation function 162 calculates a correlation coefficient using the pixel values for the respective pixel indexes in the region R22 and the pixel values for the respective pixel indexes in the region R23 as bivariate data. Thereafter, the calculation function 162 calculates the first index value of the (n+1)th frame by subtracting the calculated correlation coefficient from "1".

As described above, the calculation function 162 calculates the first index value of the nth frame and the (n+1)th frame for the pixel position $(x_k, y_k)$ in the ROI. The calculation function 162 also calculates the first index value for each of all the pixel positions in the ROI by performing the same processing on the other pixel positions in the ROI. The calculation function 162 also performs the same processing on the other B-mode images in the N-sheets of B-mode images, to calculate a plurality of first index values arranged in time series. The calculated first index values are associated with the frame numbers (time phase) and/or the pixel positions and stored in the storage circuitry 150 and/or a memory (not illustrated).

In FIG. 7, the value "1−correlation coefficient" is defined as the first index value to define the index value increasing as fluctuations increases. By the definition, the size relation of the first index value is linked with the magnitude relation of fluctuations. This structure enables drawing, with high luminance, of a region (pixel) having large fluctuations when the data is output as a parametric image described later. However, the first index value is not always limited to the value "1−correlation coefficient". For example, the calculation function 162 may output the value of the correlation coefficient as the first index value without any processing. In this case, although the size relation of the first index value and the magnitude relation of fluctuations have reversed relation, the value can be used as an index value indicating the degree of fluctuations. As another example, the calculation function 162 may define the first index value using a statistical value indicating similarity (difference) between the image signals. For example, the calculation function 162 may calculate, as the first index value, a correlation coefficient, the value "1–correlation coefficient", the absolute coefficient, the value "1–absolute coefficient", a sum of absolute differences (SAD), or a sum of squared differences (SSD) between the image signals in the two medical images. Specifically, in the present embodiment, the first index value indicating similarity may be a value (similarity) increasing as the degree of similarity increases, or a value (dissimilarity) increasing as the degree of difference increases. However, in the case of numeralizing similarity of regions having different signal intensities, such as the angioma and the background liver, it is preferable to use a correlation coefficient as a calculation method difficult to depend on the signal intensity. The correlation coefficient may be calculated on the basis of zero-mean normalized cross-correlation.

In addition, FIG. 7 illustrates the case of calculating the first index value using two B-mode images between adjacent frames (that is, one-frame interval) as an example, but the embodiment is not limited thereto. For example, the calculation function 162 may select two B-mode images having a desired frame interval, such as a two-frame interval and a three-frame interval, as an image pair, and calculate the first index value using the image pair.

In addition, FIG. 7 illustrates the case of calculating the first index value using a kernel formed of 3×3 pixels (9 pixels), as an example, but the embodiment is not limited thereto. The number of pixels included in the kernel may be set as desired. For example, the calculation function 162 may calculate the first index value using a kernel of 1×1 pixel (1 pixel) as a kernel of the minimum unit.

At Step S208, the calculation function 162 calculates a second index value on the basis of the first index values in each of the pixel positions. For example, the calculation function 162 calculates a second index value corresponding to the statistical value in the time direction of the first index values, on the basis of the first index values calculated for the respective image pairs. Specifically, the calculation function 162 calculates the second index value of each of the positions using the first index values corresponding to each of the positions in the region of interest.

The following is an explanation of the processing at Step S208 with reference to FIG. 8. FIG. 8 illustrates the processing performed in the case of calculating the second index value on the basis of the time-series first index values in each of the pixel positions in the ROI (region R20) Two graphs illustrated in FIG. 8 illustrate time-series change of the first index value at a representative point in the ROI (region R20). In these graphs, the horizontal axis corresponds to the time (frame), and the vertical axis corresponds to the first index value (1–correlation coefficient).

As illustrated in FIG. 8, at the representative point of the background liver, because the correlation coefficient is comparatively high (close to 1) in each of the frames, the first index value is low in each of the frames. By contrast, at the representative point of the angioma, because the correlation coefficient is often lower than that of the background liver, the first index value is generally higher than that in the background liver. For this reason, the calculation function 162 calculates a statistical value in the time direction of the first index values as the second index value. Specifically, the second index value can be regarded as an index value relating to the state of the angioma.

For example, the calculation function 162 calculates a standard deviation in the time direction of the first index values, as the second index value. In this manner, the calculation function 162 calculates a second index value for each of the pixel positions in the ROI (region R20). The calculated second index value is associated with the pixel position and stored in the storage circuitry 150 and/or a memory (not illustrated).

FIG. 8 illustrates the case of calculating a standard deviation as the second index value, but the embodiment is not limited thereto. For example, the calculation function 162 may calculate dispersion, an average value, the median, a correlation coefficient, the absolute coefficient, or a moving average value of the first index values in the time direction, as the second index value. In the case of calculating a moving average value, it is preferable to hold and output the maximum value or the minimum value of the moving average values calculated in the time direction. The calculation function 162 is not always required to calculate the statistical value in the time direction of the first index values, as the second index value. For example, the calculation function 162 may calculate a difference (for example, a difference between first index values adjacent in the time direction) between first index values, as the second index value.

The following is an explanation of FIG. 4 again. At Step S105, the generation function 163 generates a parametric image. For example, the generation function 163 generates a parametric image indicating spatial distribution of the second index values. The parametric image is an example of the index image.

The following is an explanation of the processing at Step S105 with reference to FIG. 9. FIG. 9 illustrates an example of a parametric image generated with the generation function 163. FIG. 9 illustrates the case of generating a parametric image I10 on the basis of the second index values calculated for the ROI (region R20) of FIG. 8.

As illustrated in FIG. 9, the generation function 163 generates a parametric image I10 by assigning pixel values (colors) corresponding to the magnitudes of the second index values in the respective pixel positions included in the ROI (region R20) to the respective pixel positions in the ROI. Specifically, a high-luminance region R24 in the parametric image I10 suggests existence of an angioma.

The parametric image I10 is preferably displayed to be superimposed on a B-mode image 120 serving as a background image. An image of any frame in the N-sheets of B-mode images can be properly selected as the B-mode image 120.

At Step S106, the output control function 164 displays the parametric image. For example, the output control function 164 displays the parametric image I10 generated with the generation function 163 on the display 103. Thereafter, the processing circuitry 160 ends the processing.

The processes illustrated in FIG. 4 and FIG. 5 are mere examples, and not limited to the illustrated processes. For example, the smoothing processing at Step S201 is not always executed.

In addition, for example, FIG. 4 illustrates the case where a parametric image is displayed as an example of the output form, but the embodiment is not limited thereto. For example, the output control function 164 may output a representative value of the second index values. In this case, the calculation function 162 calculates a representative value of a measurement region corresponding to at least part of the ROI, on the basis of the second index values of the respective positions in the measurement region. For example, when the operator sets the region R24 in FIG. 9 as the measurement region, the calculation function 162 calculates a representative value using the second index values of the respective pixels in the region R24. The representative value is a statistical value, such as an average value, the median, the maximum value, and the minimum value. The output control function 164 displays the representative value of the region R24 calculated with the calculation function 162 on the display 103.

In addition, for example, the output control function 164 may display a histogram of the second index values. The histogram is, for example, a graph having the vertical axis indicating frequency (number of pixels) and the horizontal axis indicating the magnitude of the second index value.

Specifically, the output control function 164 is capable of outputting the second index values in the output form properly selected from the parametric image, the representative value, and the histogram, and the like. The output destination of the output from the output control function 164 is not limited to the display 103. For example, the output control function 164 may store information of the output target in the storage circuitry 150, or transmit the information to an external device.

As described above, in the ultrasonic diagnostic apparatus 1 according to the first embodiment, the acquisition function 161 acquires a plurality of time-series medical images. The calculation function 162 calculates a first index value indicating similarity between image signals in two medical images for each of image pairs, each of which is formed of two medical images included in the medical images. The calculation function 162 also calculates a second index value on the basis of the first index values calculated for the respective image pairs. This structure enables the ultrasonic diagnostic apparatus 1 to evaluate change of signal intensity of each time period.

For example, the ultrasonic diagnostic apparatus 1 calculates a first index value on the basis of "strength of correlation (similarity) between frames". In addition, the ultrasonic diagnostic apparatus 1 calculates a second index value on the basis of "relation of correlations in the frame direction". This structure enables the ultrasonic diagnostic apparatus 1 to quantitatively evaluate change of signal intensity of each time period.

As an example, there are cases where the operator (doctor) finds a region (shadow) suspected of an angioma in the B-mode image. In such a case, the operator displays a parametric image on the display 103 using the ultrasonic diagnostic apparatus 1 according to the first embodiment. In this operation, as illustrated in the region R24 of FIG. 9, when a region is emphasized with a luminance value equal to or higher than a predetermined value, the operator is enabled to determine that change of signal intensity of each time period is recognized in the region. As a result, the operator is enabled to determine that the shadow in the B-mode image is an angioma. This structure enables the operator to more conveniently recognize an angioma by ultrasonic scan of the B-mode images without performing recognition using ultrasonic contrast. Accordingly, the ultrasonic diagnostic apparatus 1 enables recognition of an angioma even in routine inspection.

First Modification of the First Embodiment

For example, FIG. 9 illustrates the case of generating the parametric image I10 on the basis of the second index values, but the embodiment is not limited thereto. For example, the generation function 163 may generate a plurality of parametric images indicating spatial distribution of the first index values. The parametric images are images (parametric images of similarity) indicating similarity (correlation) between the frames. The output control function 164 is capable of displaying a plurality of generated parametric images of similarity side by side or in the time-series order.

For example, the generation function 163 assigns pixel values according to the magnitude of the first index values to the respective pixel positions, to generate parametric images of similarity. Because the first index values are time-series information, parametric images of similarity are a plurality of images (moving images) arranged in time series. In parametric images of similarity, the region in which an angioma exists is drawn with comparatively high luminance. In addition, when moving images of the parametric images of similarity are played back, a change in which the luminance value increases and decreases is recognized in the region in which an angioma exists.

The first index values are not limited to parametric images of similarity, but may be output as a graph. For example, the output control function 164 displays a graph (graph similar to those in FIG. 8) illustrating time-series change of the first index values in a desired position designated by the operator on the display 103.

In addition, the first index values are not limited to parametric images of similarity or a graph, but can be output in the output form, such as a representative value and a histogram. The output forms of a representative value and a histogram are the same as the output forms of the representative value of the second index values and the histogram described above, and an explanation thereof is omitted.

Second Modification of the First Embodiment

As another example, the output control function 164 may display scatter diagrams as illustrated in FIG. 2 and FIG. 3.

For example, when the operator designates a point on the B-mode image, the generation function 163 sets a kernel including the designated point serving as the center. The generation function 163 generates a plurality of scatter diagrams arranged in time series by plotting points corresponding to respective pixel positions in the kernel between the adjacent frames. When N-sheets of B-mode images exist, N−1 scatter diagrams are generated. Thereafter, the output control function 164 displays the generated scatter diagrams side by side or in the time-series order. For example, in a position (point) in which an angioma exists, scatter diagrams like SP11 to SP13 are displayed. By contrast, in a position in which no angioma exists, scatter diagrams like SP21 to SP23 are displayed.

This structure enables the operator to check strength of correlation on the scatter diagrams. This structure also enables the operator to check whether the correlation in the scatter diagrams changes in the frame direction by viewing the scatter diagrams in the frame direction. Consequently, this structure enables the operator to determine whether an angioma exists in the designated position.

Third Modification of the First Embodiment

As another example, an indicator indicating the minimum scanning time can be displayed in imaging of B-mode images, to sufficiently secure the number of frames of the B-mode images used for calculation of the second index values.

For example, when the operator brings the ultrasonic probe 101 into contact with the body surface of the subject P and starts ultrasonic scan, an indicator is displayed. The indicator may have a form of, for example, performing countdown in accordance with the minimum scanning time, or may have a form of performing notification when the minimum scanning time has passed.

Second Embodiment

The first embodiment described above has illustrated the case of using the first index values of all the frames as the calculation target of the second index value, but the embodiment is not limited thereto. For example, the ultrasonic diagnostic apparatus 1 may calculate a second index value using first index values of frames designated as the calculation target in N-sheets of B-mode image data. For example, when movement of a property that cannot be completely corrected by motion stabilizer processing, it is preferable to designate frames serving as the calculation target.

For example, when the whole tissue drawn in the image uniformly performs translational movement, it is possible to detect and correct the movement of the tissue as displacement by the motion stabilizer processing. However, living tissue does not always perform uniform translational movement. For example, also in the case where the tissue in the image is influenced by beats, the tissue may include a region easily influenced by beats and a region difficult to be influenced by beats. In such a case, because the tissue in the image does not perform uniform translational movement, the movement is not completely corrected even by motion stabilizer processing, but remains. As described above, in the case where movement (hereinafter referred to as "residual tissue movement") of the tissue remaining even after motion stabilizer processing exists, recognition of a region in which an angioma exists becomes difficult.

Figure 10:
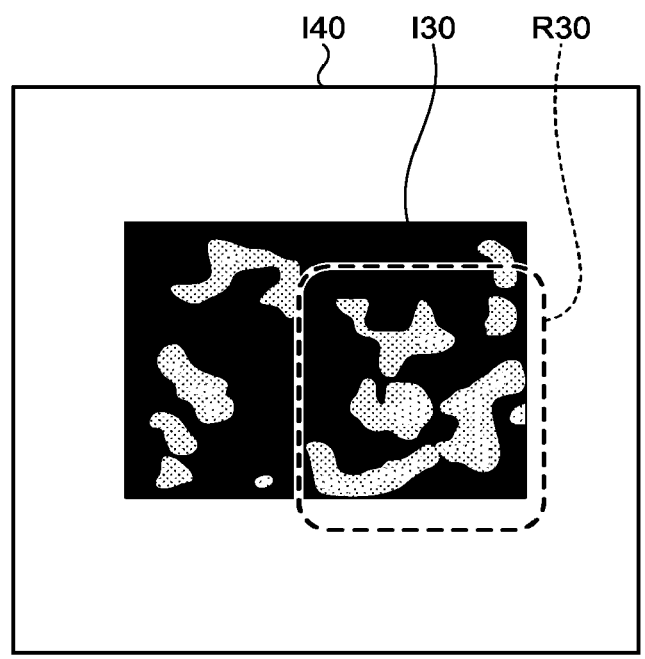
FIG. 10 is a diagram illustrating an example of a parametric image in the case where residual tissue movement is included.

The following is an explanation of a parametric image in the case of including residual tissue movement with reference to FIG. 10. FIG. 10 is a diagram illustrating an example of a parametric image in the case of including residual tissue movement. A parametric image 130 is displayed in a superimposed state on a B-mode image 140 serving as a background image.

As illustrated in FIG. 10, when residual tissue movement is included, the parametric image 130 may include a high-luminance region also in a region other than the region R30 in which an angioma exists. It is considered that this is because the value of the first index value (1−correlation coefficient) increases due to residual tissue movement.

For this reason, the second embodiment illustrates the case of calculating the second index value, excluding frames greatly influenced by residual tissue movement from the N-sheets of B-mode image data. Designating frames (reject frames) to be excluded in N-sheets of B-mode image data has substantially the same meaning as designating frames serving as the calculation target.

The ultrasonic diagnostic apparatus 1 according to the second embodiment has the same configuration as that of the ultrasonic diagnostic apparatus 1 illustrated in FIG. 1, and is different from the latter in part of the index value calculation processing illustrated in FIG. 4. For this reason, the second embodiment will be explained mainly with respect to points different from the first embodiment, and an explanation of the structure explained in the first embodiment is omitted.

Figure 11:
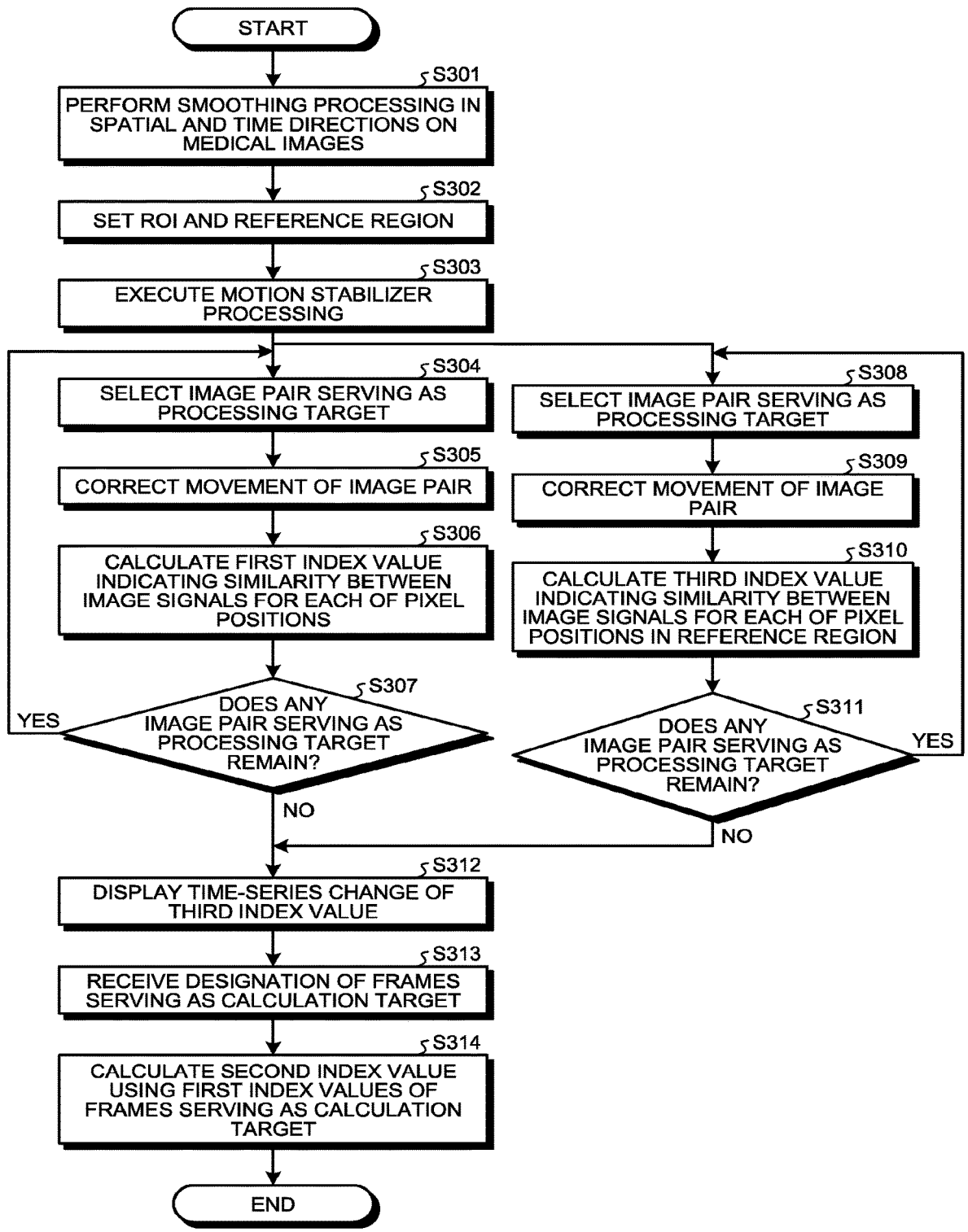
FIG. 11 is a flowchart illustrating a process of index value calculation processing according to a second embodiment.

The following is an explanation of a process performed with the ultrasonic diagnostic apparatus 1 according to the second embodiment with reference to FIG. 11. FIG. 11 is a flowchart illustrating a process of index value calculation processing according to the second embodiment. The process illustrated in FIG. 11 corresponds to the processing details at Step S104 illustrated in FIG. 4.

Figure 12:
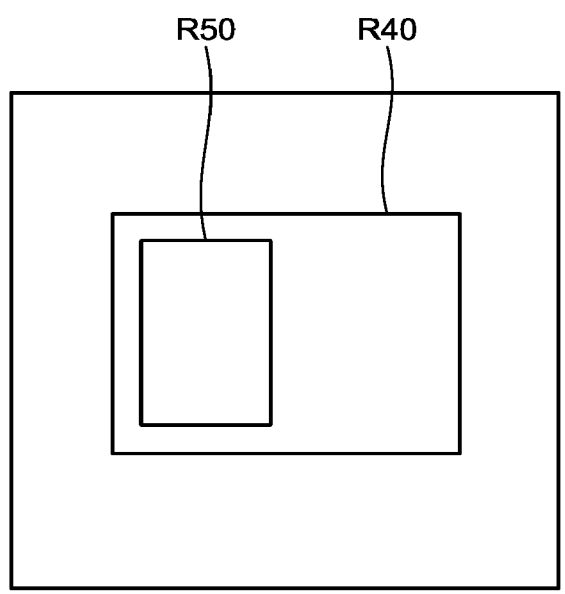
FIG. 12 is a diagram for explaining processing of setting a reference region according to the second embodiment.
Figure 13:
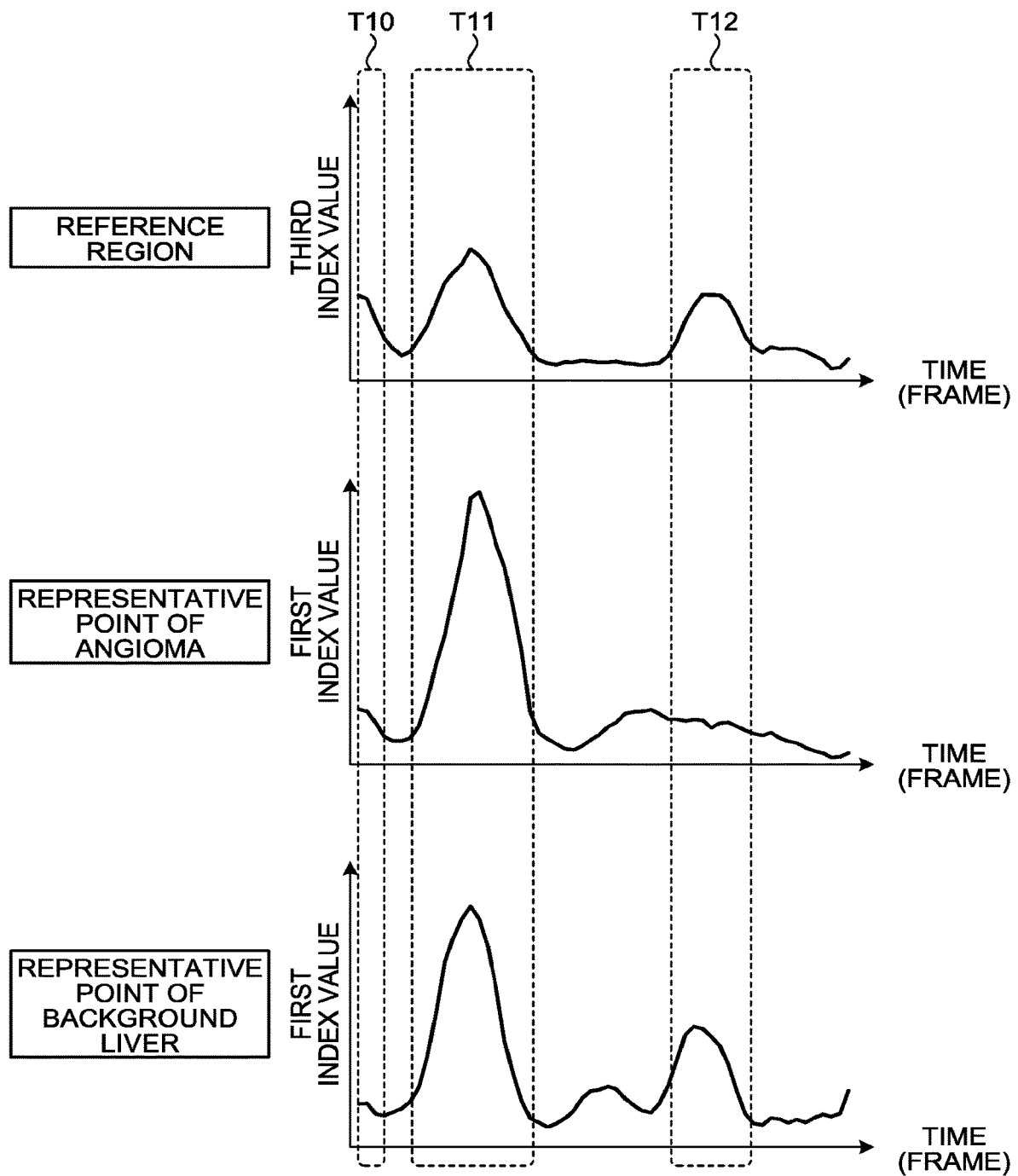
FIG. 13 is a diagram illustrating an example of time-series change of a third index value according to the second embodiment.
Figure 14:
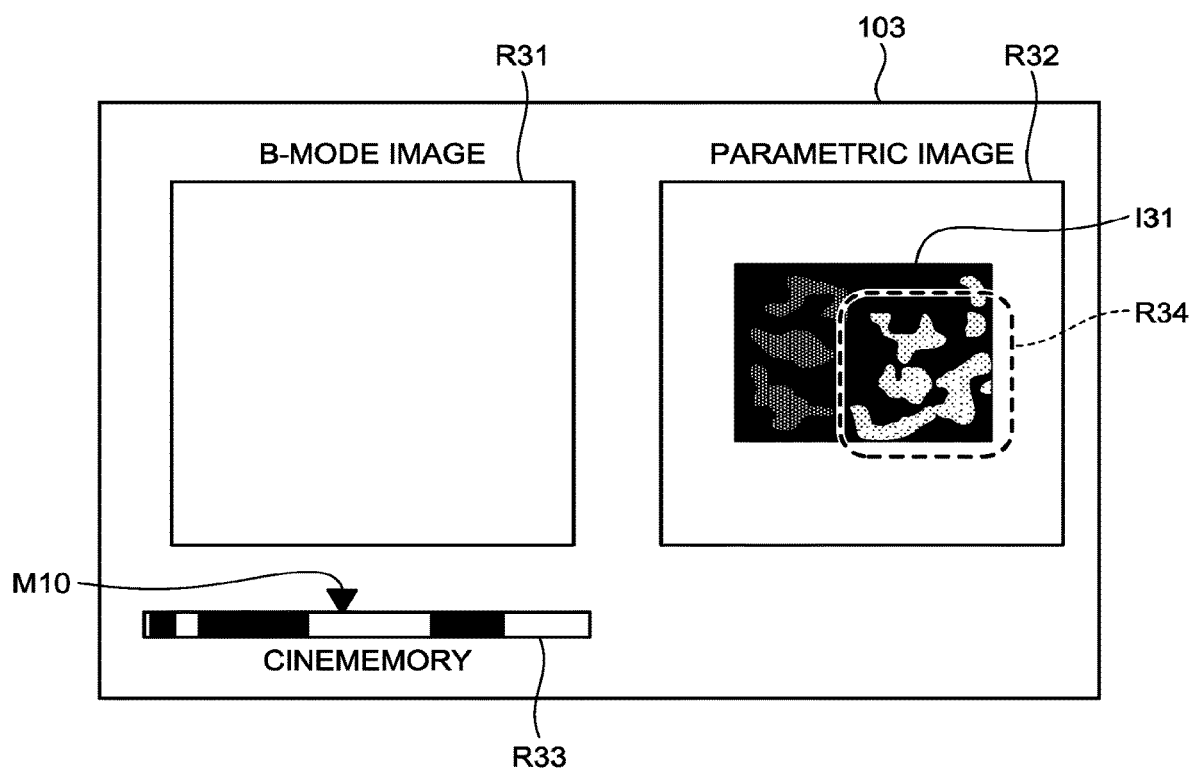
FIG. 14 is a diagram illustrating an example of a display image according to the second embodiment.

In addition, the following explanation is made with reference to FIG. 12 to FIG. 14. FIG. 12 is a diagram for explaining processing of setting a reference region according to the second embodiment. FIG. 13 is a diagram illustrating an example of time-series change of a third index value according to the second embodiment.

At Step S301, the calculation function 162 performs smoothing processing in the spatial direction in the time direction on a plurality of medical images. The processing at Step S301 is the same as the processing at Step S201 illustrated in FIG. 5, and an explanation thereof is omitted.

At Step S302, the calculation function 162 sets a ROI and a reference region. For example, as illustrated in FIG. 12, the calculation function 162 displays a B-mode image (typically, an image of the first frame) being one of smoothed N-sheets of B-mode images on the display 103. The operator designates a region including a region suspected of an angioma and a non-suspected region (background liver) on the B-mode image, as the ROI (region R40). The operator also designates a region of the background liver as a reference region (region R50). The calculation function 162 sets the regions designated by the operator on the B-mode image, as the ROI and the reference region. The calculation function 162 also sets a ROI and a reference region in the other B-mode images (for example, images of the second to the nth frames) on the basis of the ROI and the reference region of the first frame. A region having a size approximately several times as large as the size of the speckle is preferably set as the reference region.

This example illustrates the case where the ROI and the reference region are manually set, but they may be automatically set. For example, the calculation function 162 may extract the contour of the structure in the image by publicly known segmentation processing, and set the ROI and the reference region in the image on the basis of the position and/or the shape of the extracted contour.

At Step S303, the calculation function 162 performs motion stabilizer processing. The processing at Step S303 is the same as the processing at Step S203 illustrated in FIG. 5, and an explanation thereof is omitted.

Thereafter, when Step S303 is finished, the calculation function 162 performs processing at Step S308 to Step S311 in parallel with processing at Step S304 to Step S307. The processing at Step S308 to Step S311 is processing of calculating a third index value indicating similarity between the image signals. The processing at Step S304 to Step S307 is the same as the processing at Step S204 to Step S207 illustrated in FIG. 5, and an explanation thereof is omitted.

At Step S308, the calculation function 162 selects an image pair serving as the processing target. This processing is the same as the processing at Step S104 illustrated in FIG. 5, and an explanation thereof is omitted.

At Step S309, the calculation function 162 corrects movement of the image pair. This processing is the same as the processing at Step S105 illustrated in FIG. 5, and an explanation thereof is omitted.

At Step S310, the calculation function 162 calculates a third index value indicating similarity between the image signals for the reference region.

For example, the explanation illustrates the case where B-mode images of the nth frame and the (n+1)th frame are selected as the image pair serving as the processing target. In this case, the calculation function 162 calculates a third index value of the nth frame on the basis of a correlation coefficient between the image signal in the reference region of the nth frame and the image signal in the reference region of the (n+1)th frame.

For example, pixel indexes to identify the pixel positions are assigned to the respective pixel positions in the reference region. For this reason, the calculation function 162 calculates a correlation coefficient using pixel values of the respective pixel indexes in the reference region in the nth frame and pixel values of the respective pixel indexes in the reference region in the (n+1)th frame as bivariate data. Thereafter, the calculation function 162 calculates the third index value of the nth frame by subtracting the calculated correlation coefficient from "1".

At Step S311, the calculation function 162 determines whether any image pair serving as the processing target remains. For example, when any unprocessed B-mode image exists in the N-sheets of B-mode images, the calculation function 162 determines that an image pair serving as the processing target remains (Yes at Step S311), and proceeds to the processing at Step S308. By contrast, when no unprocessed B-mode image exists in the N-sheets of B-mode images, the calculation function 162 determines that no image pair serving as the processing target remains (No at Step S311), and proceeds to the processing at Step S312.

Specifically, the calculation function 162 repeatedly performs the processing from Step S308 to Step S311 while changing the image pair serving as the processing target, to successively calculate a third index value based on each of the image pairs.

As described above, the calculation function 162 calculates a plurality of third index values arranged in time series, on the basis of the respective reference regions of the N-sheets of B-mode images. The calculated third index values are associated with the frame numbers (time phases) and stored in the storage circuitry 150 and/or a memory (not illustrated).

In FIG. 11, the value "1−correlation coefficient" is defined as the third index value, but the structure is not limited thereto. For example, the calculation function 162 may calculate, as the third index value, a correlation coefficient, the value "1−correlation coefficient", the absolute coefficient, the value "1−absolute coefficient", SAD, or SSD between the image signals in the two medical images. However, the same definition as the definition of the first index value is preferably used as the definition of the third index value.

At Step S312, the output control function 164 displays time-series change of the third index value. For example, the output control function 164 reads a plurality of third index values calculated with the calculation function 162 and arranged in time series from the storage circuitry 150. Thereafter, the output control function 164 generates a graph indicating the time-series change of the third index value on the basis of the read third index values arranged in time series, and displays the graph on the display 103.

At Step S313, the calculation function 162 receives designation of frames serving as the calculation target. For example, the operator views the graph indicating the time-series change of the third index value displayed on the display 103, and performs an input to designate frames (reject frames) to be excluded from the calculation target. The calculation function 162 receives the input to designate the reject frames.

The following is an explanation of selection of frames serving as the calculation target according to the second embodiment, with reference to FIG. 13. The upper part of FIG. 13 illustrates a graph illustrating time-series change of the third index value in the reference region. The middle part of FIG. 13 illustrates a graph illustrating time-series change of the first index value in the representative point of the angioma. The lower part of FIG. 13 illustrates a graph illustrating time-series change of the first index value in the representative point of the background liver. In the graphs of FIG. 13, the horizontal axis corresponds to time, and the vertical axis corresponds to the first index value or the third index value (that is, the value "1−correlation coefficient").

As illustrated in the upper part of FIG. 13, the time-series change of the third index value in the reference region indicates movement of the whole tissue including the background liver. Specifically, the graphs illustrates that movement of the whole tissue is large in the frame with a large third index value, and movement of the whole tissue is small in the frame with a small third index value.

In the case where the residual tissue movement is small (movement of the whole tissue can be generally corrected by motion stabilizer processing), the third index value of the reference region should be small. However, when any frame with the large third index value in the reference region exists, it proves that the frame includes residual tissue movement. For example, because the third index value is large in a period T10, a period T11 and a period T12, it is considered that residual tissue movement exists in the frames (upper part of FIG. 13).

In addition, residual tissue movement may also influence the signal intensity of the angioma and/or the background liver therearound. For example, the first index value in the representative point of the angioma and/or the representative point of the background liver is generally large in the period T10, the period T11, and the period T12 (middle part and lower part of FIG. 13). In addition, the curves of the first index value included in the period T10, the period T11, and the period T12 are similar to curve shapes of the third index value in the same periods. These facts suggest that regions in which an angioma and/or the background liver exist are influenced by residual tissue movement. Accordingly, frames including residual tissue movement can be regarded as undesirable frames as the calculation target.

For this reason, the output control function 164 displays a graph (graph in the upper part of FIG. 13) illustrating time-series change of the third index value on the display. The output control function 164 may generate and display not only the graph illustrating time-series change of the third index value but also a graph illustrating time-series change of the first index value in the position designated by the operator. In this case, the operator may designate a position considered to include an angioma and/or a position considered to include no angioma, as desired.

The operator performs an input to designate frames included in the period T10, the period T11, and the period T12 as reject frames. In this manner, the calculation function 162 receives the input to designate the frames included in the period T10, the period T11, and the period T12 as reject frames. This example illustrates the case where the operator designates the reject frames, but the operator may designate frames serving as the calculation target.

At Step S314, the calculation function 162 calculates the second index value using the first index values of the frames serving as the calculation target. For example, the calculation function 162 sets the first index values of the frames included in the period T10, the period T11, and the period T12 in the N-sheets of B-mode images to "null".

Thereafter, the calculation function 162 calculates the second index value using the first index values of the frames other than the period T10, the period T11, and the period T12.

As described above, the ultrasonic diagnostic apparatus 1 according to the second embodiment calculates the second index value, excluding the first index values of frames greatly influenced by residual tissue movement in the N-sheets of B-mode images from the calculation target. With this structure, the ultrasonic diagnostic apparatus 1 is enabled to calculate the second index value more accurately.

The following is an explanation of a display image according to the second embodiment with reference to FIG. 14. FIG. 14 is a diagram illustrating an example of the display image according to the second embodiment. FIG. 14 illustrates a display image in the case of including residual tissue movement. In FIG. 14, a region R31 is a region to cinedisplay the B-mode image. A region R32 is a region to display a parametric image, and a B-mode image of a desired time phase is displayed in the region R32 as a background image of the parametric image. A region R33 is a region to display a bar indicating a cinememory.

As illustrated in FIG. 14, the output control function 164 displays a parametric image 131 on the display 103. Because a region R34 in the parametric image 131 includes pixels of high luminance, it is suggested that the region R34 includes an angioma. In addition, because no angioma exists in the outside of the region R34, the outside of the region R34 is drawn with low luminance.

As described above, the ultrasonic diagnostic apparatus 1 according to the second embodiment is capable display the region R34 including an angioma and a region (outside of the region R34) including no angioma such that the regions are clearly distinguished from each other, even when residual tissue movement exists therein.

The output control function 164 also display information indicating the reject frames. For example, the output control function 164 displays positions corresponding to the reject frames in the bar indicating the cinememory of the region R33 with black regions. The black regions indicate frames corresponding to the period T10, the period T11, and the period T12 of FIG. 13. This structure enables the operator to recognize the reject frames on the bar indicating the cinememory.

The black regions indicating the reject frames are not always required to be black, but may be displayed with a color or hatching to be distinguished from the other regions. In addition, the information indicating the reject frames is not always displayed on the bar indicating the cinememory. For example, the information may be displayed on the display 103 as a numerical value indicating the imaging time and the frame number.

As another example, frames serving as the calculation target may be displayed, instead of displaying the reject frames. The information indicating the frames serving as the calculation target can be displayed in the same display form as that of the information indicating the reject frames.

The second embodiment illustrates the case of performing the processing (Step S304 to Step S307) of calculating the first index value in parallel with the processing (Step S308 to Step S311) of calculating the third index value, but the embodiment is not limited thereto. For example, the ultrasonic diagnostic apparatus 1 may perform the processing of calculating the third index value after performing the processing of calculating the first index value, or perform the processing of calculating the first index value after performing the processing of calculating the third index value.

In addition, in the case of performing the processing of calculating the first index value after performing the processing of calculating the third index value, the first index value may be calculated with the B-mode images, from which the reject frames have been excluded, serving as the processing target. In this case, the calculation function 162 selects an image pair (processing at Step S304) serving as the processing target from B-mode images, from which the reject frames have been excluded. Thereafter, the calculation function 162 performs the processing at Step S305 and Step S306 on the selected image pair, and determines whether any image pair serving as the processing target remains (processing at Step S307). In the processing at Step S307, when an unprocessed B-mode image remains in the B-mode images, from which the reject frames have been excluded, the calculation function 162 determines that an image pair serving as the processing target remains. By contrast, when no unprocessed B-mode image remains in the B-mode images, from which the reject frames have been excluded, the calculation function 162 determines that no image pair serving as the processing target remains. With this structure, because no processing of calculating the first index value is performed on frames that do not serve as the calculation target, the ultrasonic diagnostic apparatus 1 is enabled to reduce the load of the processing of calculating the first index value.

Modification of the Second Embodiment

The second embodiment has illustrated the case where the operator manually designates the reject frames, but the embodiment is not limited thereto. For example, the ultrasonic diagnostic apparatus 1 is also capable of automatically determining the reject frames.

Specifically, in the ultrasonic diagnostic apparatus 1 according to a modification of the second embodiment, the calculation function 162 sets a reference region in each of two medical images. Thereafter, the calculation function 162 calculates a third index value indicating similarity between image signals in the two medical images for the reference region. The calculation function 162 determines frames serving as the calculation target in the medical images on the basis of the third index value. Thereafter, the calculation function 162 calculates the second index value using the first index values of the frames serving as the calculation target.

For example, the calculation function 162 according to the modification of the second embodiment performs processing of determining frames serving as the calculation target on the basis of the third index value, instead of the processing at Step S313 of FIG. 11. The calculation function 162 is not always required to perform the processing (processing at Step S312) of displaying time-series change of the third index value, but time-series change of the third index value is preferably displayed to present the grounds for determining the reject frames to the operator.

In this operation, when movement of the whole tissue is properly corrected, the third index value is considered to have the following two characteristics.

The first characteristic is that "the third index value does not increase to be equal to or higher than a certain value". This is based on an inference that no difference equal to or higher than a certain value does not exist, when movement of the whole tissue has been corrected, although a certain difference may exist. For this reason, frames having a third index value equal to or higher than an average value thereof are excluded.

The second characteristic is that "the third index value does not fluctuate". Specifically, a standard deviation of the third index value should fall within a certain range. For this reason, frames having a standard deviation of the third index value equal to or larger than an average value of the standard deviation are excluded.

For this reason, the calculation function 162 determines frames satisfying both the first characteristic and the second characteristic as the calculation target. For example, the calculation function 162 sets a first threshold on the basis of the first characteristic "the third index value does not increase to be equal to or higher than a certain value". The calculation function 162 also sets a second threshold on the basis of the second characteristic "the third index value does not fluctuate". Thereafter, the calculation function 162 determines frames serving as the calculation target on the basis of comparison between the third index value and each of the first threshold and the second threshold.

Figure 15:
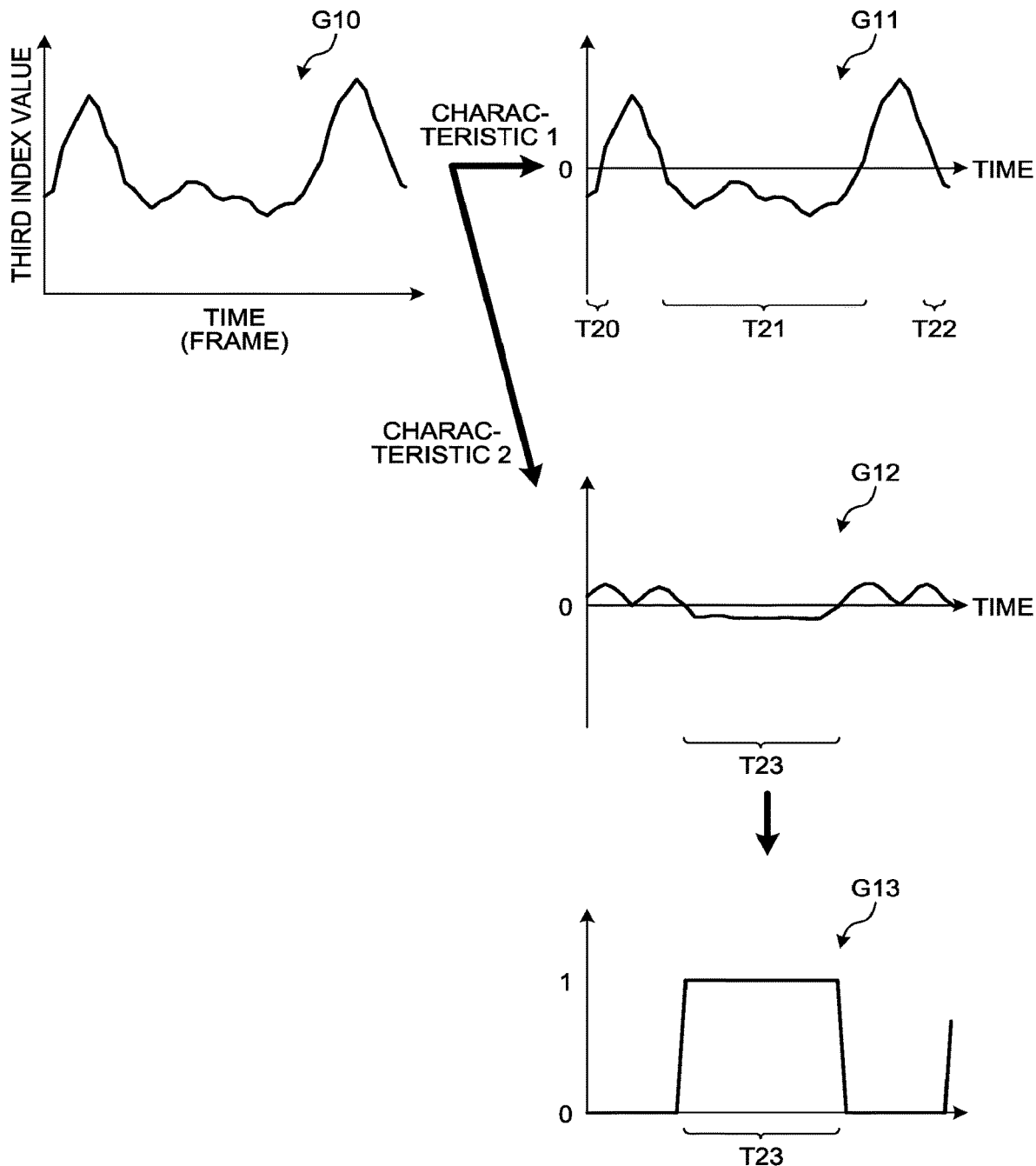
FIG. 15 is a diagram for explaining processing performed with a calculation function according to a modification of the second embodiment.

The following is an explanation of processing performed with the calculation function 162 according to the modification of the second embodiment with reference to FIG. 15. FIG. 15 is a diagram for explaining the processing performed with the calculation function 162 according to the modification of the second embodiment. A graph G10 is a graph indicating time-series change of the third index value. The processing of generating the graph is the same as the processing according to the second embodiment described above, and an explanation thereof is omitted.

For example, the calculation function 162 calculates an average value of the third index values of all the frames as the first threshold, on the basis of the first characteristic. Thereafter, the calculation function 162 compares the third index values with the first threshold. For example, the calculation function 162 subtracts the value of the first threshold from the third index value of each of the frames in the graph G10, to generate a graph G11. In the graph G11, the horizontal axis corresponds to time, and the vertical axis corresponds to the subtraction value. The position of "0" in the vertical axis corresponds to the first threshold.

Thereafter, the calculation function 162 excludes frames each having a value larger than the first threshold. Specifically, the calculation function 162 excludes frames each having a value larger than "0" of the graph G11, and leaves frames included in a period T20, a period T21, and a period T22.

The calculation function 162 also calculates an average value of standard deviations of the third index values of all the frames as the second threshold, on the basis of the second characteristic. Thereafter, the calculation function 162 compares the third index values with the second threshold. For example, the calculation function 162 subtracts the value of the second threshold from the standard deviation of the third index value of each of the frames, to generate a graph G12. The standard deviation of the third index value of each of the frames is calculated as a standard deviation of third index values for several frames before and after each of the frames. In the graph G12, the horizontal axis corresponds to time, and the vertical axis corresponds to the subtraction value. The position of "0" in the vertical axis corresponds to the second threshold.

Thereafter, the calculation function 162 excludes frames each having a value larger than the second threshold. Specifically, the calculation function 162 excludes frames each having a value larger than "0" of the graph G12, and leaves frames included in a period T23.

In this operation, frames satisfying both the first characteristic and the second characteristic are frames left in both the graph G11 and the graph G12. Because the period T23 is included in the period T21, frames satisfying both the first characteristic and the second characteristic in FIG. 15 are frames included in the period T23. For example, when the frames satisfying both the first characteristic and the second characteristic are indicated with the value "1" and frames failing to satisfy the characteristics are indicated with the value "0", a graph G13 of FIG. 15 is obtained. Specifically, the calculation function 162 determines the frames included in the period T23 as the calculation target.

As described above, the ultrasonic diagnostic apparatus 1 according to the modification of the second embodiment is capable of automatically determining frames serving as the calculation target. The explanation described above illustrates the case where frames satisfying both the first characteristic and the second characteristic are set as the calculation target, but the embodiment is not limited thereto. For example, the calculation function 162 may determine frames satisfying at least one of the first characteristic and the second characteristic as the calculation target. In addition, the first threshold and the second threshold described above are mere examples, and any thresholds may be set. However, the threshold is preferably a value based on a statistical value in the time direction of the third index values.

Third Embodiment

The first and the second embodiments described above have illustrated the case of calculating similarity (first index value) of a point (center position) on the basis of image signals in the kernel, and paying attention to change of similarity in the frame direction. However, a half width of correlation coefficient distribution depends on a point spread function (PSF) of the image system. For example, when the PSF is wide, because the correlation coefficient distribution has a large width even when there is a change due to fluctuations in the frame direction, decrease of the correlation coefficient is smaller than estimated decrease, and the discrimination for fluctuations may decrease.

For this reason, the third embodiment illustrates the case of improving the discrimination for fluctuations in the frame direction by providing a search region to pay attention to change of correlation coefficient distribution (distribution of similarity) in a two-dimensional space in the frame direction, not paying attention to a correlation coefficient of a point.

The ultrasonic diagnostic apparatus 1 according to the third embodiment has the same configuration as that of the ultrasonic diagnostic apparatus 1 illustrated in FIG. 1, and is different in part of the index value calculation processing illustrated in FIG. 5. For this reason, the third embodiment mainly illustrates points different from the first embodiment, and an explanation of the structures described in the first embodiment is omitted.

Figure 16:
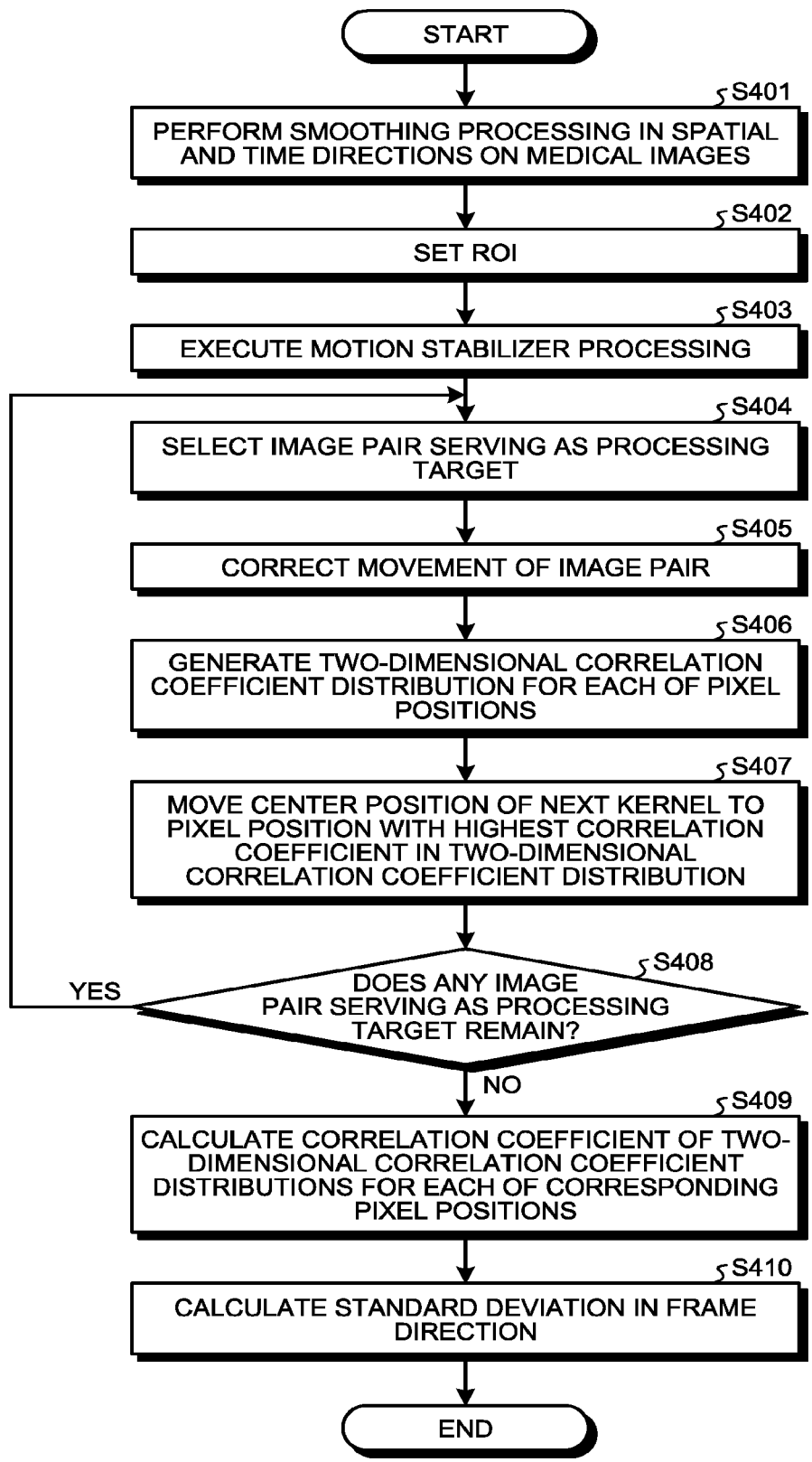
FIG. 16 is a flowchart illustrating a process of index value calculation processing according to a third embodiment.

The following is an explanation of a process performed with the ultrasonic diagnostic apparatus 1 according to the third embodiment with reference to FIG. 16. FIG. 16 is a flowchart illustrating a process of index value calculation processing according to the third embodiment. The process illustrated in FIG. 16 corresponds to the processing details (that is, the processing details of FIG. 5) at Step S104 illustrated in FIG. 4.

Figure 17:
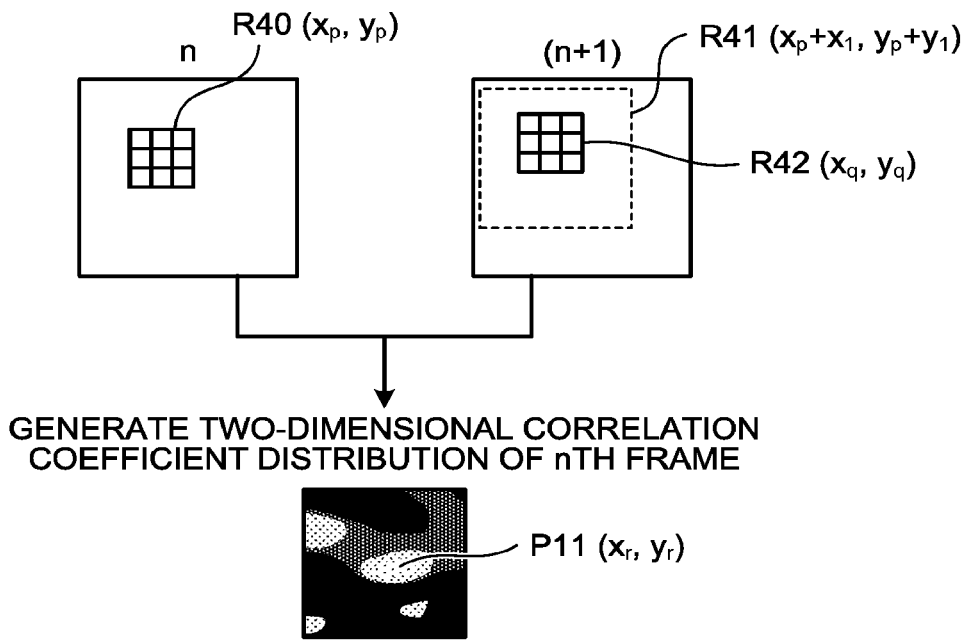
FIG. 17 is a diagram for explaining processing of generating two-dimensional correlation coefficient distribution according to the third embodiment.
Figure 18:
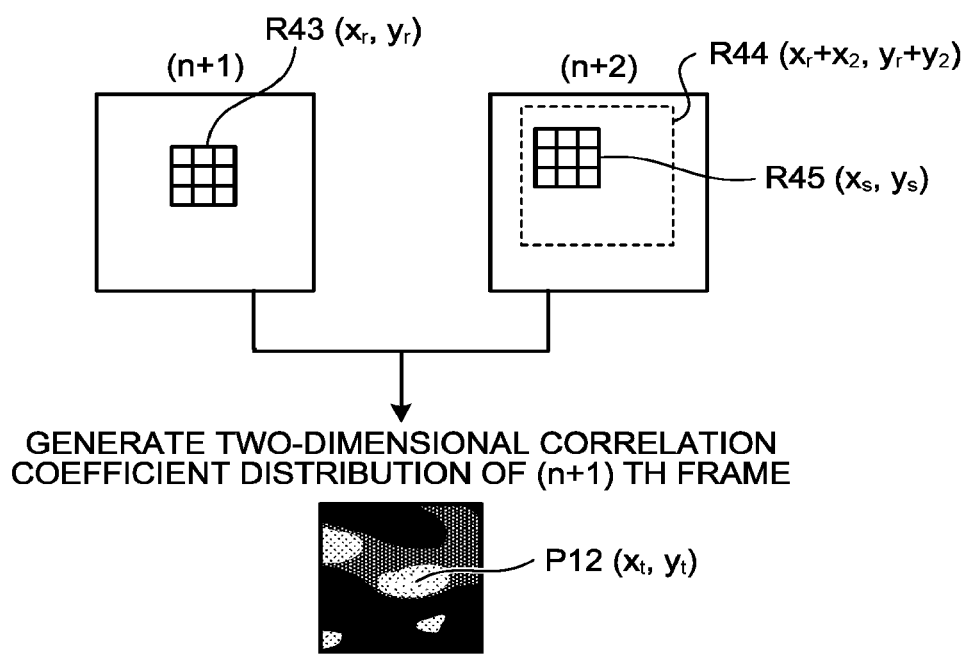
FIG. 18 is a diagram for explaining processing of generating two-dimensional correlation coefficient distribution according to the third embodiment.
Figure 19:
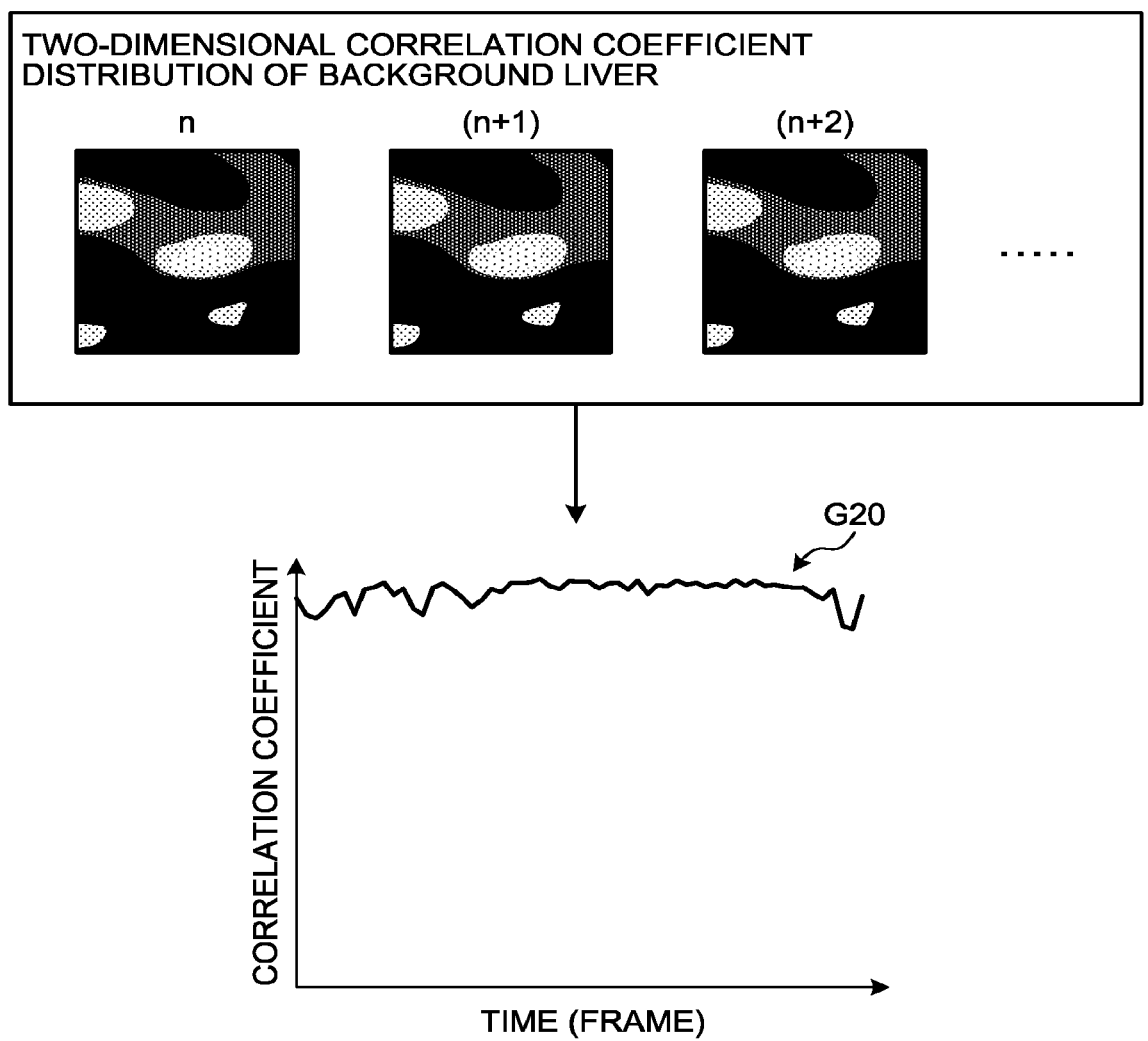
FIG. 19 is a diagram for explaining processing of calculating a correlation coefficient of the two-dimensional correlation coefficient distributions according to the third embodiment.
Figure 20:
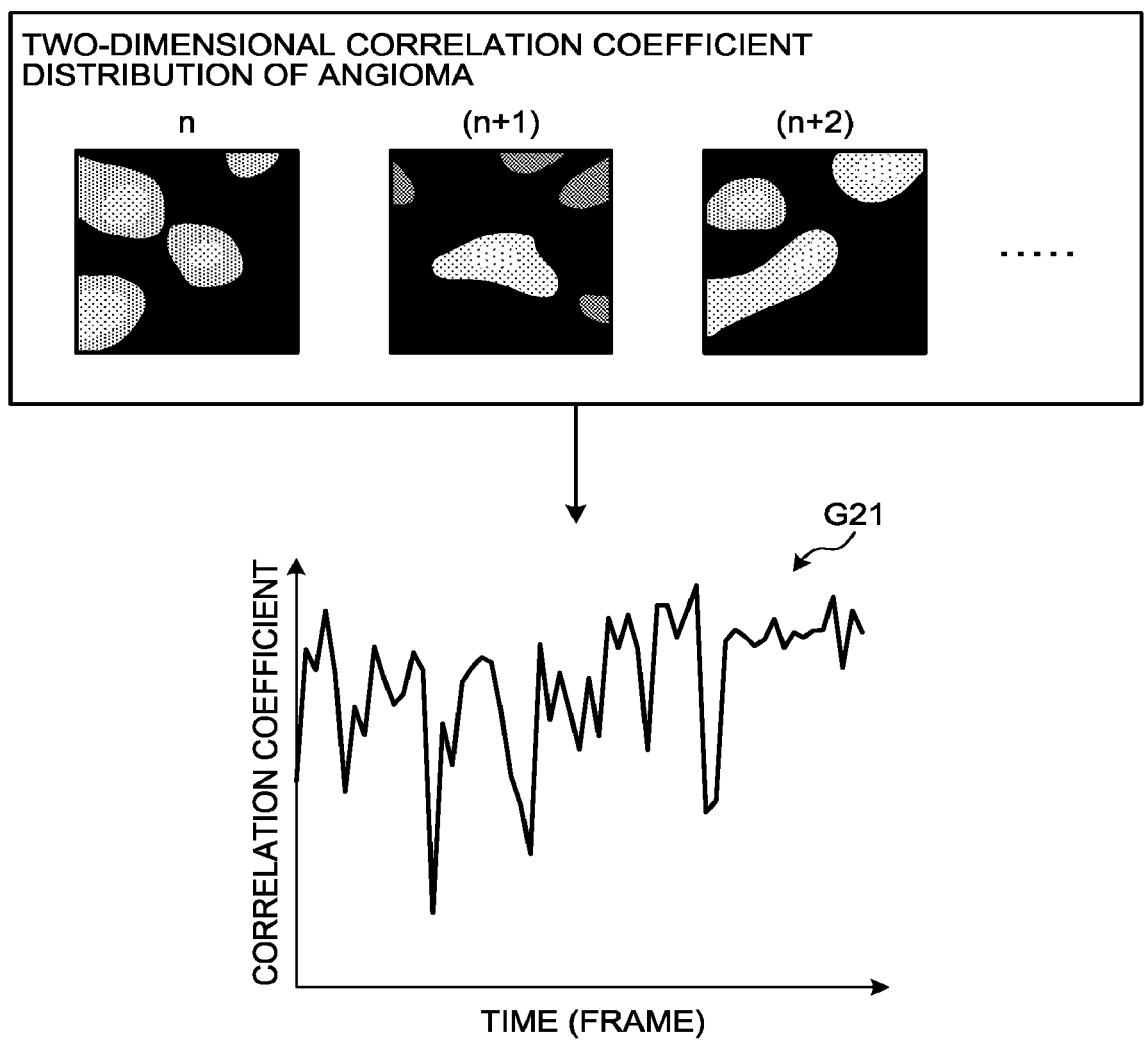
FIG. 20 is a diagram for explaining processing of calculating a correlation coefficient of the two-dimensional correlation coefficient distributions according to the third embodiment.

The following explanation is made with reference to FIG. 17 to FIG. 20. FIG. 17 and FIG. 18 are diagrams for explaining processing of generating two-dimensional correlation coefficient distribution according to the third embodiment. FIG. 19 and FIG. 20 are diagrams for explaining processing of calculating correlation coefficients of two-dimensional correlation coefficient distribution according to the third embodiment.

At Step S401 to Step S405, the calculation function 162 performs each processing. The processing at Step S401 to Step S405 is the same as the processing at Step S201 to Step S205 illustrated in FIG. 5, and an explanation thereof is omitted.

At Step S406, the calculation function 162 generates two-dimensional correlation coefficient distribution for each of the pixel positions. Specifically, for each of image pairs each formed of two medical images included in a plurality of medical images, the calculation function 162 calculates an index value group (fourth index value group) indicating similarity between an image signal in each of positions in one medical image and an image signal in each of a plurality of positions in the other image. The two-dimensional correlation coefficient distribution is an example of an index value group.

At Step S407, the calculation function 162 moves the center position of the next kernel to the pixel position with the highest correlation coefficient in the two-dimensional correlation coefficient distribution.

At Step S408, the calculation function 162 determines whether any image pair serving as the processing target remains. For example, when any unprocessed B-mode image exists in the N-sheets of B-mode images, the calculation function 162 determines that an image pair serving as the processing target remains (Yes at Step S408), and proceeds to the processing at Step S404. By contrast, when no unprocessed B-mode image exists in the N-sheets of B-mode images, the calculation function 162 determines that no image pair serving as the processing target remains (No at Step S408), and proceeds to the processing at Step S409.

Specifically, the calculation function 162 repeatedly performs the processing from Step S404 to Step S408 while changing the image pair serving as the processing target. Thereafter, the calculation function 162 successively selects image pairs, and successively calculates a first index value based on each of the image pairs.

The following is an explanation of the processing at Step S404 to Step S408 with reference to FIG. 17 and FIG. 18. FIG. 17 illustrates the processing in the case of generating two-dimensional correlation coefficient distribution of the nth frame from B-mode images of the nth frame and the (n+1)th frame. In FIG. 17, a region R40 indicates a kernel set in the B-mode image of the nth frame. A region R41 indicates a search region set in the B-mode image of the (n+1)th frame. A region R42 indicates a kernel set in the B-mode image of the (n+1)th frame. FIG. 18 illustrates processing in the case of generating two-dimensional correlation coefficient distribution of the (n+1)th frame from B-mode images of the (n+1)th frame and the (n+2)th frame. In FIG. 18, a region R43 indicates a kernel set in the B-mode image of the (n+1)th frame. A region R44 is a search region set in the B-mode image of the (n+2)th frame. A region R45 is a kernel set in the B-mode image of the (n+2)th frame.

First, the following is an explanation of the case where the B-mode images of the nth frame and the (n+1)th frame are selected as the image pair serving as the processing target, with reference to FIG. 17. In this case, the calculation function 162 sets a kernel (region R40) including a pixel position $(x_p, y_p)$ included in the ROI and serving as the center, in the B-mode image of the nth frame.

Thereafter, the calculation function 162 sets a search region (region R41) including a pixel position corresponding to the pixel position $(x_p, y_p)$ and serving as the center, in the B-mode image of the (n+1)th frame. When displacement between the images of the nth frame and the (n+1)th frame is $(x_1, y_1)$, the calculation function 162 sets a search region (region R41) including a pixel position $(x_p+x_1, y_p+y_1)$ of the B-mode image of the (n+1)th frame as the center.

Thereafter, the calculation function 162 generates two-dimensional correlation coefficient distribution between the image signal of the pixel position $(x_p, y_p)$ in the B-mode image of the nth frame and the image signal of each of pixel positions in the search region in the B-mode image signal of the (n+1)th frame. For example, the calculation function 162 sets a kernel (region R42) including a pixel position $(x_q, y_q)$ in the search region (region R41) as the center. The calculation function 162 calculates a correlation coefficient corresponding to the pixel position $(x_q, y_q)$, on the basis of the image signal in the kernel (region R40) and the image signal in the kernel (region R42). For example, the calculation function 162 calculates a correlation coefficient using the pixel values for the respective pixel indexes in the region R40 and the pixel values for the respective pixel indexes in the region R42 as bivariate data.

Thereafter, while changing the pixel position $(x_q, y_q)$ in the search region (region R41), the calculation function 162 calculates a correlation coefficient between the image signal of each of the changed pixel positions and the image signal of the pixel position $(x_p, y_p)$. In this manner, the calculation function 162 generates distribution information of the correlation coefficients between the image signal of the pixel position $(x_p, y_p)$ and the respective image signals of the pixel positions in the search region (region R41), as two-dimensional correlation coefficient distribution of the nth frame. The two-dimensional correlation coefficient distribution illustrated in FIG. 17 is illustrated by assigning luminance values corresponding to the values of the coefficients of the respective pixel positions to the respective pixel positions in the search region (region R41).

Thereafter, the calculation function 162 moves the center position of the kernel in the next frame to a pixel position with the highest correlation coefficient in the two-dimensional correlation coefficient distribution. For example, the calculation function 162 moves the center position of the kernel in the next frame to a pixel position P11 $(x_r, y_r)$ having the highest luminance in the two-dimensional correlation coefficient distribution of FIG. 17. In this operation, the coordinate system in the two-dimensional correlation coefficient distribution corresponds to the coordinate system in the B-mode image of the (n+1)th frame. For this reason, the pixel position P11 $(x_r, y_r)$ corresponds to the pixel position $(x_r, y_r)$ in the B-mode image of the (n+1)th frame. In this manner, the calculation function 162 is enabled to move (track) the pixel position $(x_p, y_p)$ of the nth frame to a position with the highest similarity in the search region of the (n+1)th frame.

The following is an explanation of the case where the B-mode images of the (n+1)th frame and the (n+2)th frame are selected as the image pair serving as the processing target, with reference to FIG. 18. For the B-mode image of the (n+1)th frame, the center position $(x_r, y_r)$ of the kernel has been set in the processing of FIG. 17. For this reason, the calculation function 162 sets a kernel (region R43) including the pixel position $(x_r, y_r)$ serving as the center, in the B-mode image of the (n+1)th frame.

The calculation function 162 sets a search region (region R44) including the pixel position corresponding to the pixel position $(x_r, y_r)$ and serving as the center, in the B-mode image of the (n+2)th frame. When displacement between the images of the (n+1)th frame and the (n+2)th frame is $(x_2, y_2)$, the calculation function 162 sets a search region (region R44) including a pixel position $(x_r+x_2, y_r+y_2)$ of the B-mode image of the (n+2)th frame as the center.

Thereafter, the calculation function 162 generates two-dimensional correlation coefficient distribution between the image signal of the pixel position $(x_r, y_r)$ in the B-mode image of the (n+1)th frame and the image signal of each of the pixel positions in the search region in the B-mode image of the (n+2)th frame. For example, the calculation function 162 sets a kernel (region R45) including a pixel position $(x_s, y_s)$ in the search region (region R44) as the center. The calculation function 162 calculates a correlation coefficient corresponding to the pixel position $(x_s, y_s)$, on the basis of the image signal in the kernel (region R43) and the image signal in the kernel (region R45). For example, the calculation function 162 calculates a correlation coefficient using the pixel values for the respective pixel indexes in the region R43 and the pixel values for the respective pixel indexes in the region R45 as bivariate data.

Thereafter, while changing the pixel position $(x_s, y_s)$ in the search region (region R44), the calculation function 162 calculates a correlation coefficient between the image signal of each of the changed pixel positions and the image signal of the pixel position $(x_r, y_r)$. In this manner, the calculation function 162 generates distribution information of the correlation coefficients between the image signal of the pixel position $(x_r, y_r)$ and the respective image signals of the pixel positions in the search region (region R44), as two-dimensional correlation coefficient distribution of the (n+1)th frame. The two-dimensional correlation coefficient distribution illustrated in FIG. 18 is illustrated by assigning luminance values corresponding to the values of the coefficients of the respective pixel positions to the respective pixel positions in the search region (region R44).

Thereafter, the calculation function 162 moves the center position of the kernel in the next frame to a pixel position with the highest correlation coefficient in the two-dimensional correlation coefficient distribution. For example, the calculation function 162 moves the center position of the kernel in the next frame to a pixel position P12 $(x_t, y_t)$ having the highest luminance in the two-dimensional correlation coefficient distribution of FIG. 18. In this operation, the coordinate system in the two-dimensional correlation coefficient distribution corresponds to the coordinate system in the B-mode image of the (n+2)th frame. For this reason, the pixel position P12 $(x_t, y_t)$ corresponds to the pixel position $(x_t, y_t)$ in the B-mode image of the (n+2)th frame.

As described above, the calculation function 162 generates two-dimensional correlation coefficient distribution of the nth frame and the (n+1)th frame while tracking the pixel position $(x_p, y_p)$ in the ROI. The calculation function 162 also performs the same processing on the other pixel positions in the ROI, to generate two-dimensional correlation coefficient distribution for each of all the pixel positions in the ROI. The calculation function 162 also performs the same processing on the other B-mode images in the N-sheets of B-mode images, to generate a plurality of two-dimensional correlation coefficient distributions arranged in time series. The generated two-dimensional correlation coefficient distributions are associated with the frame numbers (time phases) and/or the pixel positions and stored in the storage circuitry 150 and a memory (not illustrated).

At Step S409, the calculation function 162 calculates the correlation coefficient of the two-dimensional correlation coefficient distributions for each of the corresponding pixel positions. Specifically, the calculation function 162 calculates a value indicating similarity between two index value groups calculated for the two image pairs, as the first index value.

The following is an explanation of processing of calculating the correlation coefficient of two-dimensional correlation coefficient distribution, with reference to FIG. 19 and FIG. 20. FIG. 19 illustrates processing in the case of calculating the correlation coefficient using time-series two-dimensional correlation coefficient distributions at a representative point of the background liver. FIG. 20 illustrates processing in the case of calculating the correlation coefficient using time-series two-dimensional correlation coefficient distributions at a representative point of the angioma.

As illustrated in FIG. 19 and FIG. 20, for each of the pixel positions, two-dimensional correlation coefficient distributions of the nth frame, the (n+1)th frame, and the (n+2)th frame are generated. The calculation function 162 calculates a correlation coefficient between the correlation coefficient in the two-dimensional correlation coefficient distribution of the nth frame and the correlation coefficient in the two-dimensional correlation coefficient distribution of the (n+1)th frame. For example, the calculation function 162 calculates a correlation coefficient of the nth frame using the correlation coefficients for the respective pixel indexes in the two-dimensional correlation coefficient distribution of the nth frame and the correlation coefficients for the respective pixel indexes in the two-dimensional correlation coefficient distribution of the (n+1)th frame as bivariate data.

The calculation function 162 also calculates a correlation coefficient between the correlation coefficient in the two-dimensional correlation coefficient distribution of the (n+1)th frame and the correlation coefficient in the two-dimensional correlation coefficient distribution of the (n+2)th frame. For example, the calculation function 162 calculates a correlation coefficient of the (n+1)th frame using the correlation coefficients for the respective pixel indexes in the two-dimensional correlation coefficient distribution of the (n+1)th frame and the correlation coefficients for the respective pixel indexes in the two-dimensional correlation coefficient distribution of the (n+2)th frame as bivariate data.

As described above, the calculation function 162 calculates a coefficient between the pair, while changing the pair of the two-dimensional correlation coefficient distributions serving as the processing target. In this manner, the calculation function 162 generates time-series information of the correlation coefficient for each of the pixel positions.

For example, FIG. 19 illustrates the case of generating time-series information of the correlation coefficient for the representative point of the background liver. In this case, because a surrounding region including the representative point of the background liver has small fluctuations, the two-dimensional correlation coefficient distributions of the nth frame, the (n+11)th frame, and the (n+2)th frame are similar to each other. For this reason, as illustrated in a graph G20, the correlation coefficient in the representative point of the background liver is fixed at a relatively high value.

By contrast, FIG. 20 illustrates the case of generating time-series information of the correlation coefficient for the representative point of the angioma. In this case, because a surrounding region including the representative point of the angioma has large fluctuations, the two-dimensional correlation coefficient distributions of the nth frame, the (n+1)th frame, and the (n+2)th frame are different from each other in many cases. For this reason, as illustrated in a graph G21, the correlation coefficient in the representative point of the angioma tends to have a low value in comparison with the background liver, and changes in the frame direction.

As described above, the calculation function 162 calculates a plurality of correlation coefficients arranged in time series for each of all the pixel positions in the ROI. FIG. 19 illustrates the same distribution (image) as the two-dimensional correlation coefficient distributions of the nth frame, the (n+1)th frame, and the (n+2)th frame, to clarify the explanation, but actually the same distributions are rarely provided side by side.

In addition, FIG. 19 and FIG. 20 illustrate the case of calculating the correlation coefficient, but the structure is not limited thereto. The correlation coefficient calculated in the processing at Step S409 corresponds to the element "first index value indicating similarity between the image signals in two medical images) explained in the first embodiment. For this reason, the calculation function 162 may calculate the value "1−correlation coefficient", the absolute coefficient, the value "1−absolute coefficient", SAD, or SSD, instead of the correlation coefficient.

At Step S410, the calculation function 162 calculates a standard deviation in the frame direction. For example, the calculation function 162 calculates a standard deviation in the frame direction using a plurality of correlation coefficients calculated for each of the pixel positions in the ROI and arranged in time series.

The standard deviation calculated in the processing at Step S410 corresponds to the element "second index value corresponding to a statistical value in the time direction of the first index values (similarity)" explained in the first embodiment. For this reason, the calculation function 162 may calculate a variance, an average value, the median, the correlation coefficient, the absolute coefficient, or a moving average value, instead of the standard deviation.

As described above, in the ultrasonic diagnostic apparatus 1 according to the third embodiment, the calculation function 162 generates two-dimensional correlation coefficient distributions for each of the pixel positions in the ROI. Thereafter, the calculation function 162 calculates first index values indicating similarities between the two-dimensional correlation coefficient distributions. The calculation function 162 calculates a second index value in the frame direction using a plurality of first index values arranged in time series. With this structure, the ultrasonic diagnostic apparatus 1 is enabled to improve the discrimination for fluctuations in the frame direction.

Modification of the Third Embodiment

For example, the output control function 164 may further display the two-dimensional correlation coefficient distributions.

For example, when the operator designates a point on the B-mode image, the calculation function 162 generates a plurality of two-dimensional correlation coefficient distributions arranged in time series for the designated point. The output control function 164 displays the generated two-dimensional correlation coefficient distributions side by side or in the time-series order. For example, for the position (point) in which an angioma exists, the two-dimensional correlation coefficient distributions illustrated in FIG. 20 are displayed. By contrast, for the position including no angioma, the two-dimensional correlation coefficient distributions illustrated in FIG. 19 are displayed.

This structure enables the operator to check whether the correlation in each of the two-dimensional correlation coefficient distributions changes in the frame direction, by viewing the two-dimensional correlation coefficient distributions in the frame direction. Consequently, the operator is enabled to determine whether the designated position includes an angioma.

Other Embodiments

Other various embodiments may be carried out other than the embodiments described above.

Use of Signals Other than B-Mode Images

For example, the embodiments described above have illustrated the case of calculating first index values and a second index value using a plurality of time-series medical images, but the embodiments are not limited thereto. For example, the first index values and the second index value may be calculated using signal groups before generated as medical images.

Specifically, the acquisition function 161 acquires a plurality of time-series signal groups. The calculation function 162 calculates a first index value indicating similarity between signals in two signal groups, for each of signal group pairs each formed of two signal groups included in the signal groups. On the basis of first index values calculated for the respective signal group pairs, the calculation function 162 also calculates a second index value corresponding to a statistical value in the time direction of the first index values.

For example, the acquisition function 161 may acquire B-mode data before converted into B-mode images, as medical images. Specifically, the medical images may be information obtained by acquiring signal values of positions included in regions that can be scanned and correspond to medical images, for respective regions that can be scanned.

As another example, the structure is not limited to ultrasonic scan performed while the opening center is slid in the lateral direction for each ultrasonic transmission/reception, such as B-mode. For example, the ultrasonic scan may be ultrasonic scan in which the opening center is fixed during certain packets and slid in the lateral direction after the same region is transmitted and received a plurality of times. The ultrasonic scan is the same as ultrasonic scan in color Doppler, but the signal information to be used is amplitude, not a frequency. Specifically, the medical images may be information obtained by acquiring signal values of positions included in the regions that can be scanned, for respective scan lines of the regions that can be scanned. In this case, because the signal value is acquired for each of the divided regions, the frame intervals when the first index value is calculated can be narrowed to pulse repetition frequency (PRF) intervals. For this reason, because the calculation processing of the first index value has very high time resolution, it is useful in analyzing the correlation of change of the signal intensity at high flow velocity.

As another example, push pulse (acoustic radiation force) may be used and/or external excitation may be performed before the ultrasonic scan described above, to analyze a response of the tissue by the external force itself. As another example, a response generated by shear waves caused by the external force. Specifically, the medical images may be information obtained by acquiring signal values of respective positions included in the regions that can be scanned, for each of scan lines, after push pulse or external excitation.

Graph Display

As another example, the ultrasonic diagnostic apparatus 1 may display any graph in the graphs explained in the embodiments described above on the display 103. For example, the generation function 163 generates a graph based on the first index values or the second index value in a predetermined position or a region. The position or the region is designated by the operator. Thereafter, the output control function 164 displays the generated graph.

Medical Information Processing Apparatus

For example, the embodiments described above have illustrated the case where the disclosed technique is applied to the ultrasonic diagnostic apparatus 1, but the embodiments are not limited thereto. For example, the disclosed technique may be applied to a medical information processing apparatus 200. The medical information processing apparatus 200 corresponds to, for example, a workstation and/or a picture archiving communication system (PACS) viewer, and the like.

Figure 21:
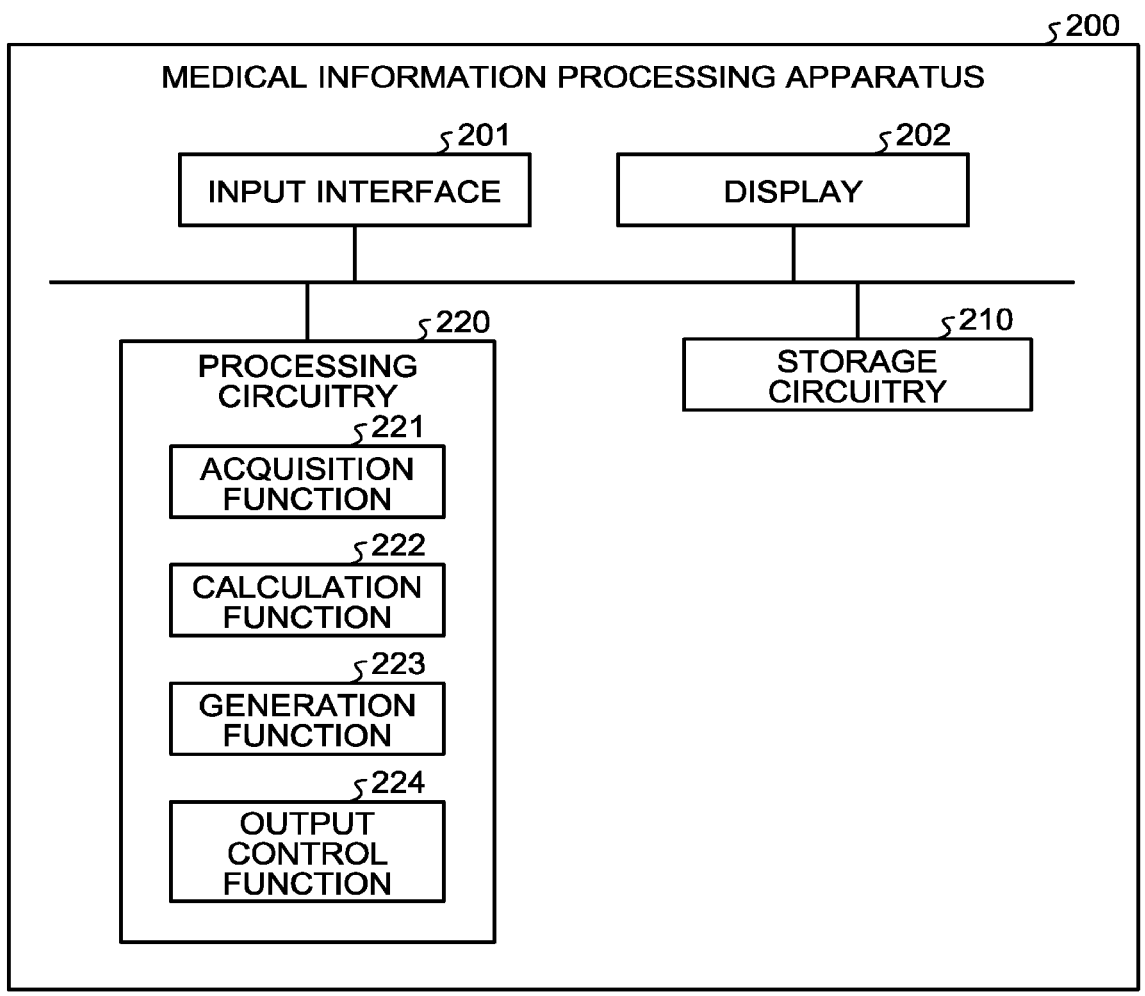
FIG. 21 is a block diagram illustrating a configuration example of a medical information processing apparatus according to another embodiment.

FIG. 21 is a block diagram illustrating a configuration example of the medical information processing apparatus 200 according to another embodiment. As illustrated in FIG. 21, the medical information processing apparatus 200 includes an input interface 201, a display 202, storage circuitry 210, and processing circuitry 220. The input interface 201, the display 202, the storage circuitry 210, and the processing circuitry 220 are mutually connected to perform mutual communications.

The input interface 201 is an input device to receive various instructions and/or setting requests from the operator, such as a mouse, a keyboard, and a touch panel. The display 202 is a display device to display medical images and/or display GUI for the operator's inputting various setting requests using the input interface 201.

The storage circuitry 210 is, for example, a not and (NAND) flash memory or a hard disk drive (HDD), and stores therein various computer programs to display medical image data and/or GUI and/or information used with the computer programs.

The processing circuitry 220 is an electronic apparatus (processor) controlling the whole processing in the medical information processing apparatus 200. The processing circuitry 220 executes an acquisition function 221, a calculation function 222, a generation function 223, and an output control function 224. The acquisition function 221, the calculation function 222, the generation function 223, and the output control function 224 are recorded, for example, in the form of computer programs executable with a computer, in the storage circuitry 210. The processing circuitry 220 reads and executes the computer programs to achieve the functions (the acquisition function 221, the calculation function 222, the generation function 223, and the output control function 224) corresponding to the read computer programs.

The acquisition function 221 is capable of performing basically the same processing as that of the acquisition function 161 illustrated in FIG. 1. The calculation function 222 is capable of performing basically the same processing as that of the calculation function 162 illustrated in FIG. 1. The generation function 223 is capable of performing basically the same processing as that of the generation function 163 illustrated in FIG. 1. The output control function 224 is capable of performing basically the same processing as that of the output control function 164 illustrated in FIG. 1.

With this structure, for example, in the medical information processing apparatus 200, the acquisition function 221 acquires a plurality of time-series medical images. The calculation function 222 calculates a first index value indicating similarity between the image signals in two medical images, for each of image pairs each formed of two medical images included in the medical images. The calculation function 222 also calculates a second index value on the basis of first index values calculated for the respective image pairs. This structure enables the medical information processing apparatus 200 to evaluate change of signal intensity of each time period.

Application to Three-Dimensional Images

As another example, the embodiments described above have illustrated the processing in the case of using two-dimensional images, but the structure is not limited thereto. The structure is also applicable to the case of using three-dimensional images (volume data).

Use of Normalized SAD or Normalized SSD

The embodiments have illustrated that the correlation coefficient, the value "1−correlation coefficient", the absolute coefficient, the value "1−absolute coefficient", SAD, or SSD described above is applicable as the first index value, but the structure is not limited thereto. For example, normalized SAD or normalized SSD is also applicable as the first index value.

For example, the calculation function 162 calculates normalized SAD "S1" using the following Expression (1). In Expression (1), the symbol "$\mathrm{Amp}_{(n)}(x_i, y_j)$" indicates the amplitude (corresponding to the pixel value) of the image signal in each of pixel positions in the kernel of the nth frame. In addition, the symbol "$\mathrm{Amp}_{(n+1)}(x_i, y_j)$" indicates the amplitude of the image signal in each of pixel positions in the kernel of the (n+1)th frame. The symbol "i" indicates an integer of 1 to k. The symbol "j" indicates an integer of 1 to l. For example, in the example of FIG. 7, each of "k" and "l" is "3".

$$S1 = \frac{\sum_{i=1}^{k} \sum_{j=1}^{l} |\mathrm{Amp}_{(n+1)}(x_i, y_j) - \mathrm{Amp}_{(n)}(x_i, y_j)|}{\sum_{i=1}^{k} \sum_{j=1}^{l} \mathrm{Amp}_{(n)}(x_i, y_j)} \quad (1)$$

The calculation function 162 also calculates normalized SSD "S2" using the following Expression (2). The symbols "$\mathrm{Amp}_{(n)}(x_i, y_j)$", "$\mathrm{Amp}_{(n+1)}(x_i, y_j)$", "i", "j", "k", and "l" in Expression (2) are the same as those in Expression (1), and an explanation thereof is omitted.

$$S2 = \frac{\sum_{i=1}^{k} \sum_{j=1}^{l} (\mathrm{Amp}_{(n+1)}(x_i, y_j) - \mathrm{Amp}_{(n)}(x_i, y_j))^2}{\sum_{i=1}^{k} \sum_{j=1}^{l} (\mathrm{Amp}_{(n)}(x_i, y_j))^2} \quad (2)$$

As described above, the calculation function 162 may calculate a value obtained by normalizing the sum of absolute differences between the image signals in the two medical images, or a value obtained by normalizing the sum of squared differences between the image signals in the two medical images, as the first index value. The processing after calculating the first index values is the same as that in the embodiments described above. Each of the values "S1" and "S2" is also referred to as "relative error".

In addition, the values "S1" and "S2" described above are also applicable as the third index value explained in the second embodiment. Specifically, the calculation function 162 may calculate a value obtained by normalizing the sum of absolute differences between the image signals in the two medical images, or a value obtained by normalizing the sum of squared differences between the image signals in the two medical images, as the third index value.

The term "processor (circuitry)" used in the explanation described above means a central processing unit (CPU), a graphics processing unit (GPU), or circuitry, such as an application specific integrated circuit (ASIC), and a programmable logic device (for example, a simple programmable logic device (SPLD), a complex programmable logic device (CPLD), and a field programmable gate array (FPGA)). The processor achieves functions by reading and executing computer programs stored in the storage circuitry 150. The computer programs may be configured to be directly incorporated into circuitry of the processor, instead of storing computer programs in the storage circuitry 150. In this case, the processor achieves functions by reading and executing the computer programs incorporated into the circuitry. Each of the processors according to the present embodiment is not limited to the case where each of the processors is formed as a single circuitry, but a plurality of independent circuits may be combined into a processor to achieve the function. As another example, a plurality of constituent elements in each of the drawings may be integrated into a processor to achieve their functions.

The constituent elements of the illustrated apparatuses are functional and conceptual ones, and are not always physically configured as illustrated. Specifically, the specific forms of distribution and integration of the apparatuses are not limited to those illustrated, but the whole or part thereof may be functionally or physically distributed or integrated in any unit according to various loads and/or use conditions. For example, the function of the image processing circuitry 130 may be integrated into the processing circuitry 160. In addition, the whole or desired part of each of the processing functions performed in the apparatuses may be achieved with a CPU and/or a computer program analyzed and executed with the CPU, or as hardware by wired logic.

In addition, in the processes explained in the embodiments described above, the whole or part of the processing explained as processing automatically performed may be manually performed, or the whole or part of the processing explained as processing manually performed may be automatically performed by a publicly known method. Besides, the processes, the control processes, the specific names, and information including various data and/or parameters illustrated in the document described above and/or drawings may be changed as desired, excluding the case specially mentioned.

The image processing method explained in the embodiments described above can be achieved by executing an image processing program prepared in advance with a computer, such as a personal computer and a workstation. The image processing program can be distributed through a network, such as the Internet. The image processing program can also be recorded in a computer-readable recording medium, such as a hard disk, a flexible disk (FD), a CD-ROM, a MO, and a DVD, and executed by being read from the recording medium with a computer.

At least one of the embodiments described above enables evaluation of change of signal intensity of each time period.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An analyzing apparatus comprising processing circuitry configured to:
   acquire a plurality of time-series medical images;
   determine frames serving as a calculation target in the plurality of time-series medical images;
   for each of image pairs each formed of two medical images included in the plurality of time-series medical images, calculate a first index value indicating similarity between image signals in the two medical images; and
   calculate, on the basis of a plurality of the first index values of the frames serving as the calculation target, a second index value corresponding to a statistical value in a time direction of the first index values calculated for the respective image pairs.

2. The analyzing apparatus according to claim 1, wherein the second index value is an index value relating to a state of an angioma.

3. The analyzing apparatus according to claim 1, wherein the processing circuitry:
   sets a region of interest for each of the two medical images; and
   calculates, using the first index values corresponding to each of a plurality of positions in the region of interest, the second index value for each of the positions.

4. The analyzing apparatus according to claim 1, further comprising processing circuitry configured to generate a first index image indicating spatial distribution of a plurality of the second index values.

5. The analyzing apparatus according to claim 4, further comprising processing circuitry configured to display the first index image.

6. The analyzing apparatus according to claim 5, wherein the processing circuitry:
   further generates a plurality of second index images indicating spatial distributions of the first index values; and
   further displays the second index images side by side or in a time-series order.

7. The analyzing apparatus according to claim 5, wherein the processing circuitry:
   generates a graph based on the first index values or the second index value in a predetermined position or region; and
   displays the graph.

8. The analyzing apparatus according to claim 1, wherein the processing circuitry calculates, as the first index value, a correlation coefficient, a value "1−correlation coefficient", an absolute coefficient, a value "1−absolute coefficient", a sum of absolute differences, a sum of squared differences, a value obtained by normalizing the sum of absolute differences, or a value obtained by normalizing the sum of squared differences between image signals in the two medical images.

9. The analyzing apparatus according to claim 1, wherein the processing circuitry calculates, as the second index value, a standard deviation, a variance, an average value, a median, a correlation coefficient, or an absolute coefficient in the time direction of the first index values.

10. The analyzing apparatus according to claim 1, wherein the processing circuitry:
sets a reference region for each of the two medical images;
calculates a third index value indicating similarity between image signals in the two medical images, for the reference region;
determines the frames serving as the calculation target in the medical images on the basis of the third index value; and
calculates the second index value using the first index values of the frames serving as the calculation target.

11. The analyzing apparatus according to claim 10, wherein the processing circuitry calculates, as the third index value, a correlation coefficient, a value "1−correlation coefficient", an absolute coefficient, a value "1−absolute coefficient", a sum of absolute differences, a sum of squared differences, a value obtained by normalizing the sum of absolute differences, or a value obtained by normalizing the sum of squared differences between the image signals in the two medical images.

12. The analyzing apparatus according to claim 11, wherein the processing circuitry determines the frames serving as the calculation target on the basis of comparison between the third index value and a threshold.

13. The analyzing apparatus according to claim 12, wherein the processing circuitry calculates a statistical value in a time direction of a plurality of the third index values, as the threshold.

14. The analyzing apparatus according to claim 1, wherein the processing circuitry:
receives an input to designate the frames serving as the calculation target in the medical images.

15. The analyzing apparatus according to claim 1, wherein the processing circuitry:
calculates, for each of image pairs each formed of two medical images included in the medical images, a fourth index value group indicating similarities between image signals in respective positions in one medical image and image signals in respective positions in the other image; and
calculates a value indicating similarity between the two fourth index value groups calculated for two image pairs, as the first index value.

16. The analyzing apparatus according to claim 1, wherein the processing circuitry acquires, as the medical images,
information obtained by acquiring signal values of positions included in regions that can be scanned and correspond to the medical images, for respective regions that can be scanned,
information obtained by acquiring signal values of positions included in the regions that can be scanned, for respective scan lines of the region that can be scanned, or
information obtained by acquiring signal values of respective positions included in the regions that can be scanned, for each of the scan lines, after push pulse or external excitation.

17. The analyzing apparatus according to claim 1, wherein the processing circuitry:
performs movement correction processing to correct movement between images on the medical images; and
calculates the first index values using the medical images having been subjected to the movement correction processing.

18. The analyzing apparatus according to claim 1, wherein the first index value is a value increasing as similarity increases.

19. The analyzing apparatus according to claim 1, wherein the first index value is a value increasing as a difference increases.

20. An analyzing method comprising:
acquiring a plurality of time-series medical images;
determining frames serving as a calculation target in the plurality of time-series medical images;
for each of image pairs each formed of two medical images included in the plurality of time-series medical images, calculating a first index value indicating similarity between image signals in the two medical images; and
calculating, on the basis of a plurality of the first index values of the frames serving as the calculation target, a second index value corresponding to a statistical value in a time direction of the first index values calculated for the respective image pairs.

21. An analyzing apparatus comprising a processing circuitry configured to:
acquire a plurality of time-series signal groups;
determining frames serving as a calculation target in the plurality of time-series signal groups;
for each of signal group pairs each formed of two signal groups included in the plurality of time-series signal groups, calculate a first index value indicating similarity between signals in the two signal groups; and
calculate, on the basis of a plurality of the first index values of the frames serving as the calculation target, a second index value corresponding to a statistical value in a time direction of the first index values calculated for the respective signal group pairs.

* * * * *